(12) United States Patent
Masmanidis et al.

(10) Patent No.: US 9,622,676 B2
(45) Date of Patent: Apr. 18, 2017

(54) METHOD OF MAKING MICROMACHINED NEURAL PROBES

(71) Applicant: CALIFORNIA INSTITUTE OF TECHNOLOGY, Pasadena, CA (US)

(72) Inventors: Sotiris K. Masmanidis, Pasadena, CA (US); Jiangang Du, Alhambra, CA (US); Michael L. Roukes, Pasadena, CA (US); Gilles J. Laurent, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 1007 days.

(21) Appl. No.: 13/707,942

(22) Filed: Dec. 7, 2012

(65) Prior Publication Data
US 2013/0167360 A1 Jul. 4, 2013

Related U.S. Application Data

(62) Division of application No. 12/335,847, filed on Dec. 16, 2008, now Pat. No. 8,355,768.
(Continued)

(51) Int. Cl.
*A61B 5/0478* (2006.01)
*A61B 5/00* (2006.01)
(Continued)

(52) U.S. Cl.
CPC ........ *A61B 5/0478* (2013.01); *A61B 5/04001* (2013.01); *A61B 5/4041* (2013.01); *A61B 5/4839* (2013.01); *A61B 5/6848* (2013.01); *A61M 5/00* (2013.01); *A61N 1/0529* (2013.01); *A61N 1/0531* (2013.01); *H01R 43/00* (2013.01); *A61B 2562/028* (2013.01); (Continued)

(58) Field of Classification Search
CPC .............. A61B 5/0478; A61B 5/04001; A61B 5/04041; A61B 5/6848; A61N 1/0529; A61N 1/0531; A61N 1/0534; A61N 1/0551; Y10T 29/49002; Y10T 29/49117; Y10T 29/49124
See application file for complete search history.

(56) References Cited

U.S. PATENT DOCUMENTS 7,326,649 B2 * 2/2008 Rodger ................ A61N 1/0551
257/737
7,853,303 B2 12/2010 Nikumb et al.
(Continued)

FOREIGN PATENT DOCUMENTS

WO WO 2005117554 A2 * 12/2005 ......... A61B 5/04001

OTHER PUBLICATIONS

Seung et al., "A high-yield fabrication process for silicon neural probes," in IEEE Transactions on Biomedical Engineering, vol. 53, No. 2, pp. 351-354, Feb. 2006.*
(Continued)

*Primary Examiner* — Livius R Cazan
(74) *Attorney, Agent, or Firm* — The Marbury Law Group, PLLC

(57) ABSTRACT

A neural probe includes at least one shaft, at least one first electrode disposed on a first side of the at least one shaft, and at least one second electrode disposed on a second side of the at least one shaft. The at least one second electrode is separately addressable from the at least first electrode.

20 Claims, 22 Drawing Sheets

Related U.S. Application Data

(60) Provisional application No. 61/007,990, filed on Dec. 17, 2007.

(51) Int. Cl.
    *A61N 1/05*     (2006.01)
    *A61B 5/04*     (2006.01)
    *A61M 5/00*     (2006.01)
    *H01R 43/00*     (2006.01)

(52) U.S. Cl.
    CPC ....... *A61N 1/0551* (2013.01); *Y10T 29/49002* (2015.01); *Y10T 29/49117* (2015.01)

(56) References Cited

U.S. PATENT DOCUMENTS

| | | | |
|---|---|---|---|
| 2006/0276866 A1* | 12/2006 | McCreery | A61N 1/0534 607/116 |
| 2007/0123765 A1 | 5/2007 | Hetke et al. | |
| 2007/0197892 A1 | 8/2007 | Shen et al. | |

OTHER PUBLICATIONS

Pang et al., "Novel Monolithic Silicon Probes with Flexible Parylene Cables for Neural Prostheses," Microtechnologies in Medicine and Biology, 2006 International Conference on, Okinawa, 2006, pp. 64-67.*

Changlin Pang et al., "A New Multi-Site Probe Array with Monolithically Integrated Parylene Flexible Cable for Neural Prostheses," 2005 IEEE Engineering in Medicine and Biology 27th Annual Conference, Shanghai, 2005, pp. 7114-7117.*

Sui et al., A Micromachined SiO2/Silicon Neural Probe for Neural Signal Recordings, Chin. Phys. Lett., vol. 23, No. 7, 2006, pp. 1932-1934.*

J. F. Hetke abd D.J. Anderson, "Silicon microelectrodes for extracellular recording," in Handbook of Neuroprosthetic Methods, W. E. Finn and P.G. LoPresti, Eds. CRC Press 2002.*

Bjornsson et al., "Effects of insertion conditions on tissue strain and vascular damage during neuroprosthetic device insertion," J. Neural Eng., 2006, 3:196-207.

Blanche et al., "Polytrodes: High-density silicon electrode arrays for large-scale multiunit recording," Journal of Neurophysiology, 2005, 93(5):2987-3000.

Bragin et al., "Gamma (40-100 Hz) oscillation in the hippocampus of the behaving rat," J. Neurosci., 1995, 15:47-60.

Buchwald et al., "Amplitudes of background fast activity characteristic of specific brain sites," J. Neurophysiol., 1970, 33:148-159.

Buzsáki, G., "Large-scale recording of neuronal ensembles," Nature Neuroscience, 2004, 7:446-451.

Campbell et al., "A silicon-based, three-dimensional neural interface: manufacturing processes for an intracortical electrode array," IEEE Trans. Biomed. Eng., 1991. 38:758-768.

Chen et al., "A multichannel neural probe for selective chemical delivery at the cellular level," IEEE Trans. Biomed. Eng., 1997, 44:760-769.

Cheung, K. C., "Implantable microscale neural interfaces," Biomed. Microdevices, 2007, 9:923-938.

Cheung et al., "Implantable multichannel electrode array based on SOI technology," J. Microelectromechanical Systems, 2003, 12:179-184.

Csicsvari et al., "Massively parallel recording of unit and local field potentials with silicon-based electrodes," J. Neurophysiol., 2003, 90:1314-1323.

Drake et al., "Performance of planar multisite microprobes in recording extracellular single-unit intracortical activity," IEEE Trans. Biomed. Eng., 1988, 35(9):719-732.

Gold et al., "On the origin of the extracellular action otential waveform: a modeling study," J. Neurophysiol., 2006, 95:3113-3128.

Gray et al., "Tetrodes markedly improve the reliability and yield of multiple single-unit isolation from multi-unit recordings in cat striate cortex," J. Neurosci. Methods, 1995, 63:43-54.

Harrison et al., "A low-power low-noise CMOS amplifier for neural recording applications," IEEE J Solid-State Circ., 2003, 38:958-965.

Henze et al., "Intracellular features predicted by extracellular recordings in the hippocampus in vivo," J. Neurophysiol., 2000, 84:390-400.

Hoogerwerf et al., "A three-dimensional microelectrode array for chronic neural recording," IEEE Transactions on Biomedical Engineering, 1994, 41(12):1136-1146.

Ilic et al., "Preparation and characterization of platinum black electrodes," J. Mat. Sci., 2000, 35(14):3447-3457.

Laurent et al., "Encoding of olfactory information with oscillating neural assemblies," Science, 1994, 265:1872-1875.

Laurent et al., "Odorant-induced oscillations in the mushroom bodies of the locust," J. Neurosci., 1994, 14:2993-3004.

Logothetis et al., "Neurophysiological investigation of the basis of the fMRI signal," Nature, 2001, 412:150-157.

Mann et al., "Perisomatic feedback inhibition underlies cholinergically induced fast oscillations in the rat hippocampus in vitro," Neuron, 2005, 45:105-117.

McIntyre et al., "Cellular effects of deep brain stimulation: model-based analysis of activation and inhibition," J. Neurophysiol., 2004, 91:1457-1469.

Moffitt et al., "Model-based analysis of cortical recording with silicon microelectrodes," Clinical Neurophysiol., 2005, 116:2240-2250.

Mountcastle, V.B., "The columnar organization of the neocortex," Brain, 1997, 120:701-722.

Najafi et al., "A high-yield IC-compatible multichannel recording array," IEEE Trans. Electron. Devices, 1985, 32(7):1206-1211.

Najafi et al., "An implantable multielectrode array with on-chip signal processing," IEEE J. Solid-State Circuits, 1986, SC-21:1035-1044.

Najafi et al., "Scaling limitations of silicon multichannel recording probes," IEEE Trans. Biomed. Eng., 1990, 37:1-11.

Neves et al., "Development of modular multifunctional probe arrays for cerebral applications," Proc $3^{rd}$ Intl IEEE EMBS Conference Neural Eng., 2007, 104-109.

Nicolelis et al., "Reconstructing the Engram: simultaneous, multisite, many single neuron recordings," Neuron, 1997, 18:529-537.

Norlin et al., "A 32-site neural recording probe fabricated by DRIE of SOI substrates," Journal of Micromechanics and Microengineering, 2002, 12(4):414-419.

Olsson et al., "Band-tunable and multiplexed integrated circuits for simultaneous recording and stimulation with microelectrode arrays," IEEE Trans Biomed Eng, 2005, 52:1303-1311.

Pang et al., "A new multi-site probe array with monolithically integrated parylene flexible cable for neural prostheses," 27th Annual International Conference of the IEEE Engineering in Medicine and Biology Society, 2005, 7114-7117.

Perez-Orive et al., "Oscillations and sparsening of odor representations in the mushroom body," Science, 2002, 297:359-365.

Perlin et al., "The effect of the substrate on the extracellular neural activity recorded with micromachined silicon microprobes," 26th Annual International Conference of the IEEE Engineering in Medicine and Biology Society, 2004, 3:2002-2005.

Pouzat et al., "Using noise signature to optimize spike-sorting and to assess neuronal classification quality," J. Neurosci. Methods, 2002, 122:43-57.

Rutishauser et al., "Online detection and sorting of extracellularly recorded action potentials in human medial temporal lobe recordings, in vivo," J. Neurosci. Methods, 2006, 154:204-224.

Segev et al., "Recording spikes from a large fraction of the ganglion cells in a retinal patch," Nature Neurosci, 2004, 7:1155-1162.

Shoham et al., "How silent is the brain: is there a dark matter problem in neuroscience?" J. Comp. Physiol. A., 2006, 192:777-784.

(56) References Cited

OTHER PUBLICATIONS

Stieglitz et al., "Flexible BIOMEMS with electrode arrangements on front and back side as key component in neural prostheses and biohybrid systems," Sensors and Actuators B, 2002, 83:8-14.
Takeuchi et al., "3D flexible multichannel neural probe array," J. Micromech. Microeng., 2004, 14:104-107.
Wise et al., "Implantable neural microsystems," Proc IEEE, 2008, 96:1184-1202.
Wise, K.D., "Integrated sensors, MEMS, and microsystems: Reflections on a fantastic voyage," Sensors and Actuators a-Physical, 2007, 136(1):39-50.
Yao et al., "A micro-assembled low-profile three-dimensional microelectrode array for neural prosthesis applications," J. Microelectromechanical Systems, 2007, 16:977-988.

\* cited by examiner

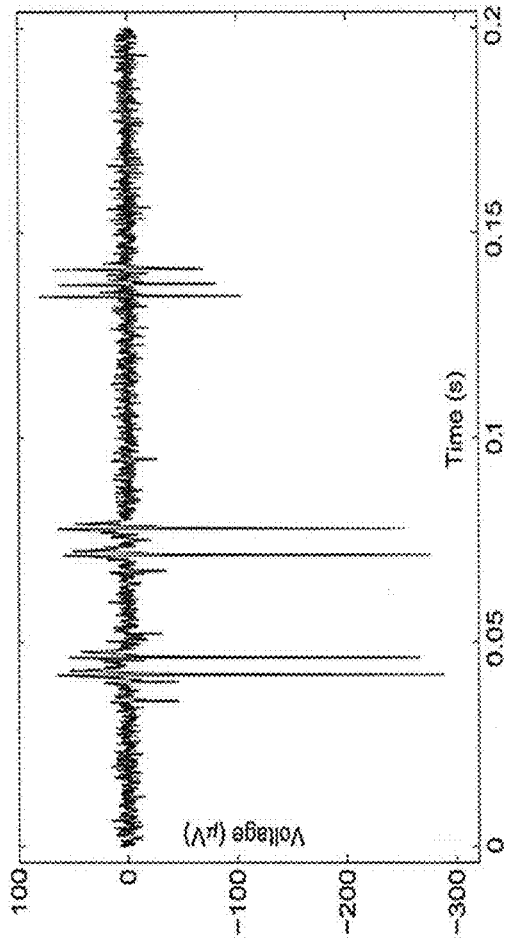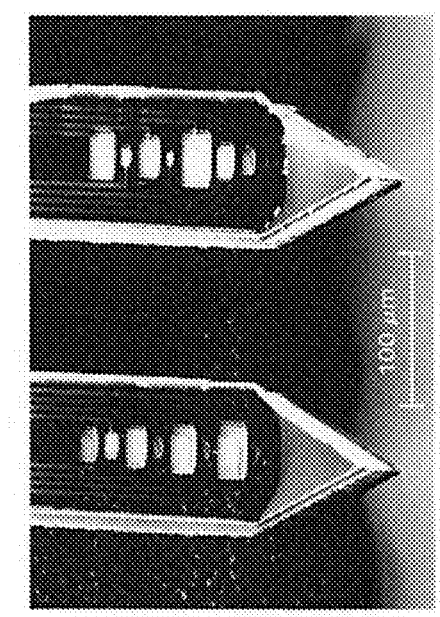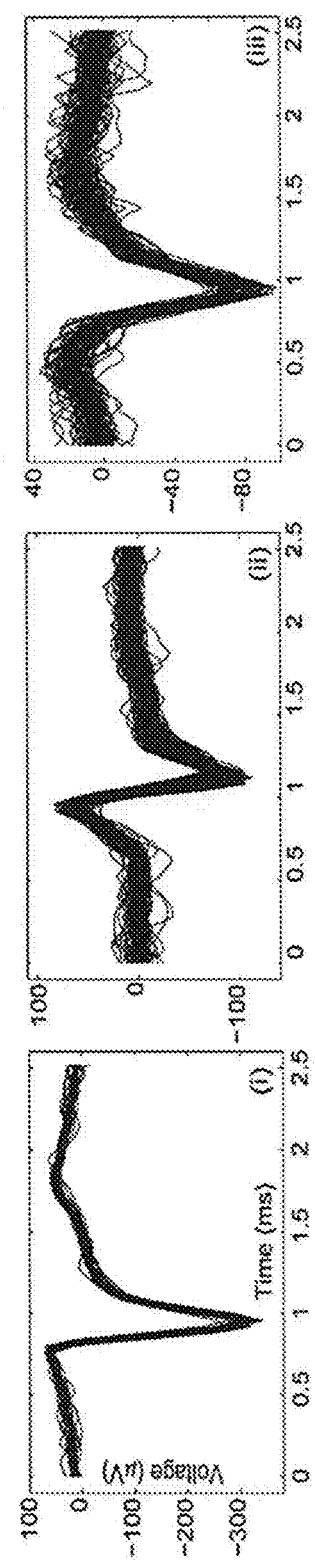
FIGURE 10A
FIGURE 10B
FIGURE 10C

601

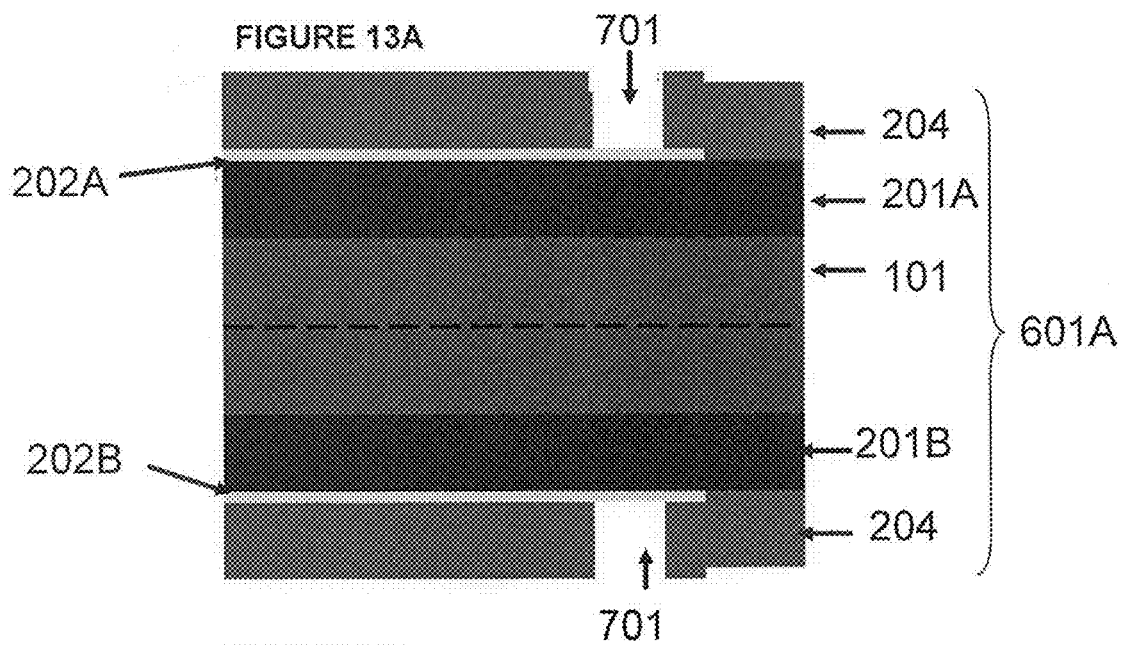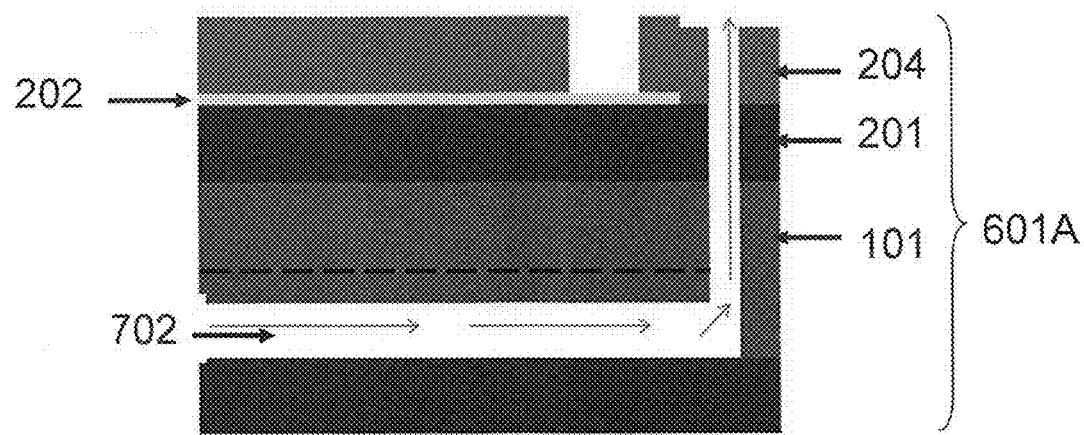

FIGURE 15A
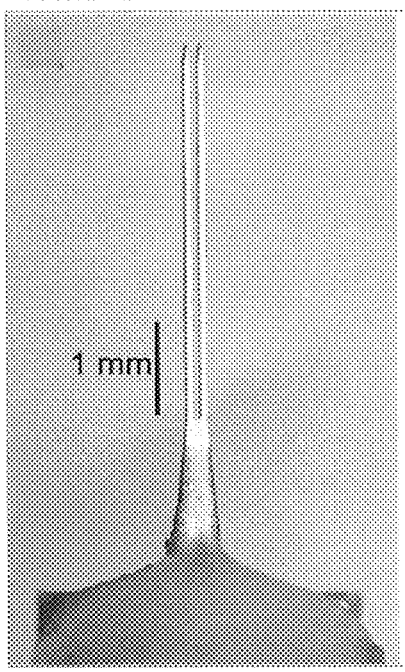
FIGURE 15B
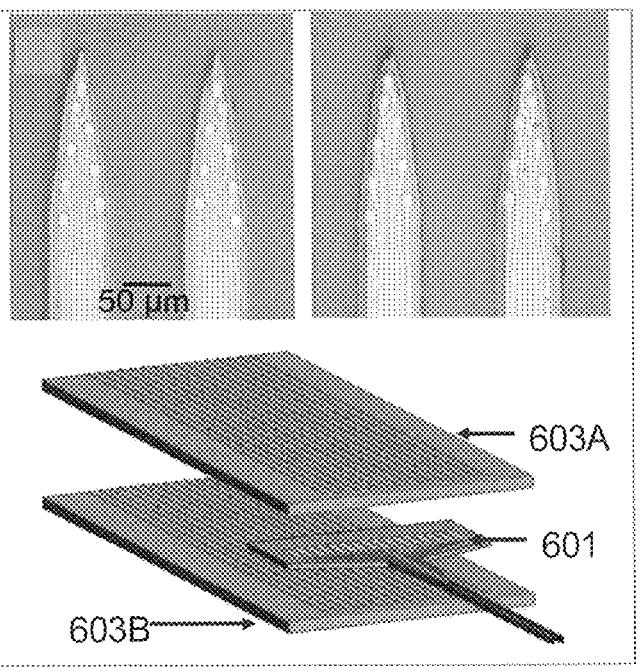
FIGURE 15C

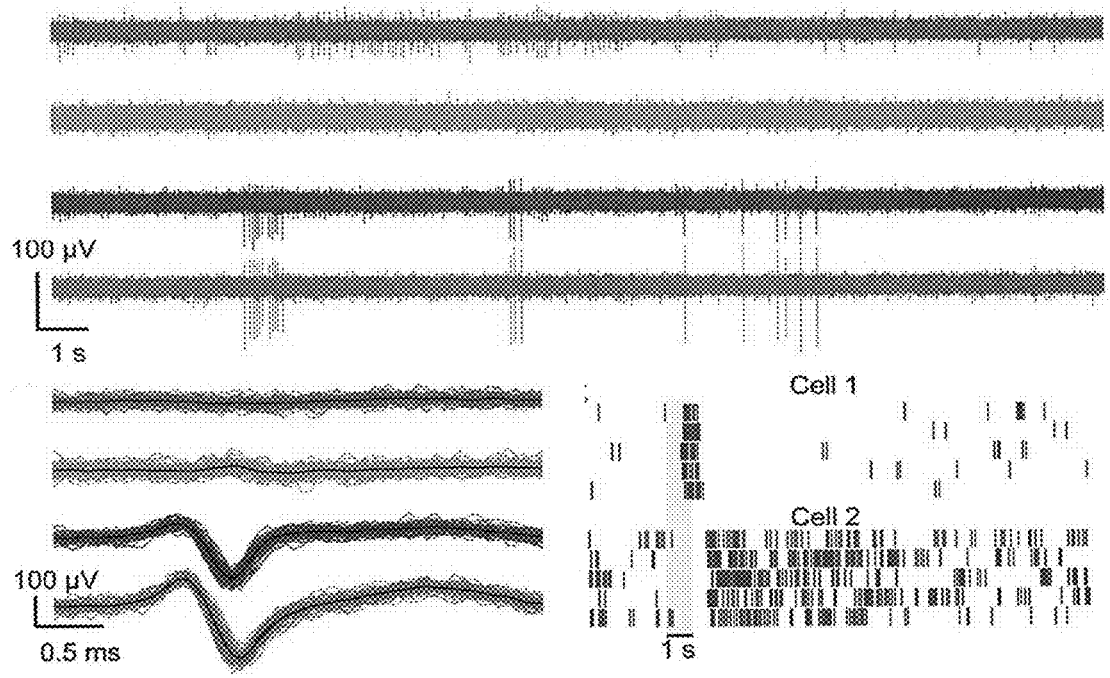

FIGURE 19A
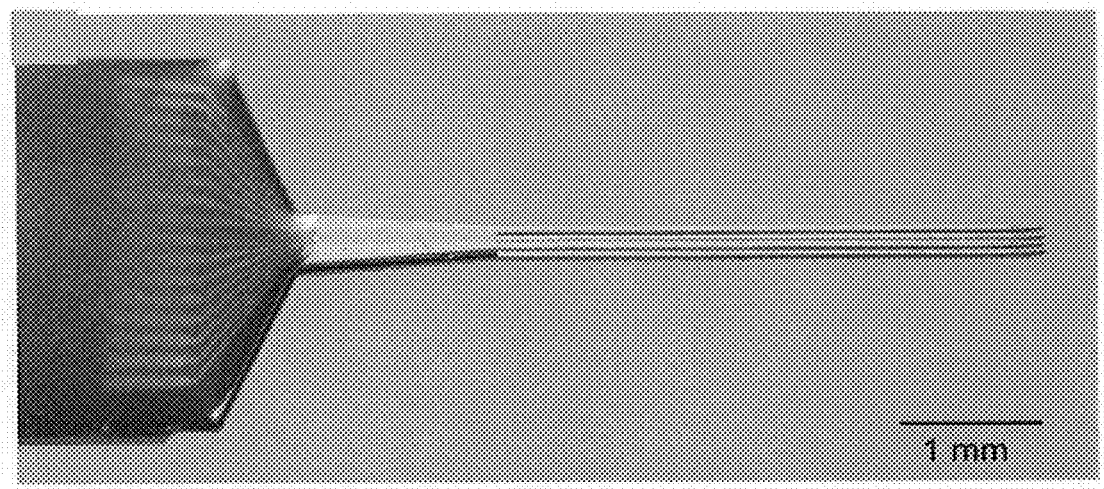
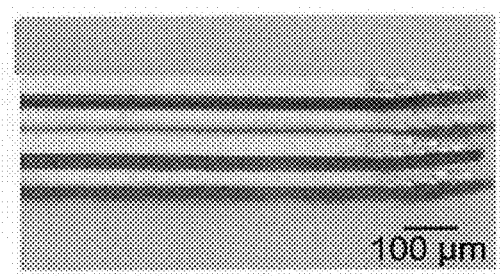
FIGURE 19B
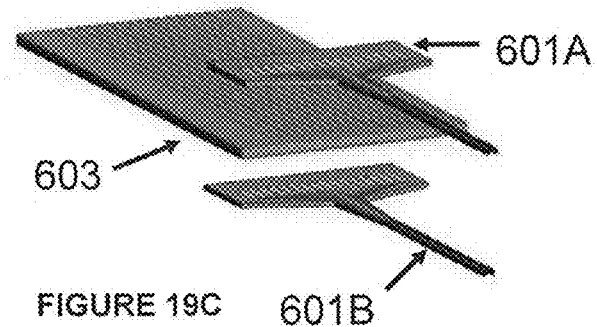
FIGURE 19C

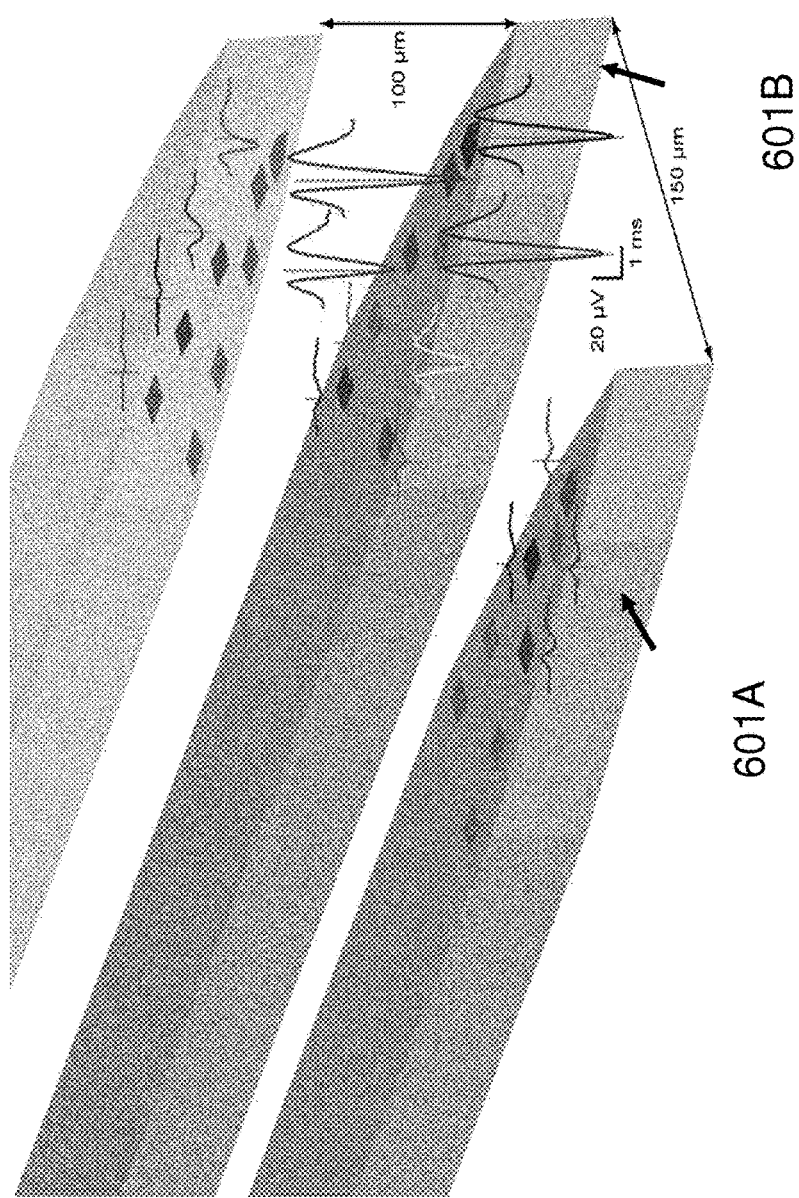

METHOD OF MAKING MICROMACHINED NEURAL PROBES

CROSS-REFERENCE TO RELATED PATENT APPLICATIONS

This application is a division of U.S. Ser. No. 12/335,847, filed Dec. 16, 2008, now U.S. Pat. No. 8,355,768, which claims priority to U.S. Provisional Application Ser. No. 61/007,990, filed Dec. 17, 2007, both of which are incorporated herein by reference in their entirety.

BACKGROUND OF THE INVENTION

The invention is related to micro-electro-mechanical systems (MEMS), and specifically to neural probes and methods of making thereof.

There is an increasing demand in neuroscience for large scale recording of neuronal activity (see Buzsáki, G., "Large-scale recording of neuronal ensembles," *Nature Neuroscience,* 2004, pp. 446-451, vol. 7). Techniques such as electroencephalography (EEG) and functional magnetic resonance imaging (fMRI) provide coarse grained views on synchronized activity, but they do not afford much insight into the brain's circuitry at the level of single neurons. The introduction of multielectrode silicon probes (see Blanche et al., "Polytrodes: High-density silicon electrode arrays for large-scale multiunit recording," Journal of Neurophysiology, 2005, pp. 2987-3000, vol. 93, no. 5; Campbell et al, "A silicon-based, three-dimensional neural interface: manufacturing processes for an intracortical electrode array," *IEEE Trans. Biomed. Eng.,* 1991. pp. 758-768; Drake et al., "Performance of planar multisite microprobes in recording extracellular single-unit intracortical activity," *IEEE Trans. Biomed. Eng.,* 1988, pp. 719-732, vol. 35, no. 9; Najafi et al., "A high-yield IC-compatible multichannel recording array," *IEEE Trans Electron Devices,* 1985, pp. 1206-1211, vol. 32, no. 7; Norlin et al., "A 32-site neural recording probe fabricated by DRIE of SOI substrates," Journal of Micromechanics and Microengineering, 2002, pp. 414-419, vol. 12, no. 4; Wise et al., "Integrated sensors, MEMS, and microsystems: Reflections on a fantastic voyage," Sensors and Actuators a-Physical, 2007, pp. 39-50, vol. 136, no. 1) has led to great advances in large scale recording with high (i.e. single-cell) resolution. However, current tools often fall short of providing a densely populated 3-dimensional 'activity map,' which may offer a better understanding of the circuitry of cell assemblies in the brain.

A need exists in the scientific and medical community to develop high recording density devices that can measure electrical multineuronal activity in the brain with single cell and spike time precision.

BRIEF SUMMARY OF THE INVENTION

One embodiment provides a neural probe, the probe comprising: at least one shaft; at least one first electrode disposed on a first side of the at least one shaft; and at least one second electrode disposed on a second side of the at least one shaft; wherein the at least one second electrode is separately addressable from the at least one first electrode.

Another embodiment provides a neural probe, the probe comprising: a first structure, comprising a first base and a first shaft extended from the first base, the first shaft comprising at least one first electrode disposed thereon; and a second structure, comprising a second base and a second shaft extended from the second base, the second shaft comprising at least one second electrode disposed on thereon, wherein the first structure is attached to the second structure, and the at least one second electrode is separately addressable from the at least one first electrode.

In another embodiment, a method of making a neural probe is provided, the method comprising providing a substrate having a thickness of less than 150 µm, such as 100 µm or less; patterning at least one first electrode on a first side of the substrate; attaching the substrate to a carrier; patterning the substrate into the neural probe comprising at least one shaft connected to a base; and removing the neural probe from the carrier.

Another embodiment provides a method of measuring extracellular potentials in a biological tissue using at least one first neural probe, comprising addressing a first electrode located on a first side of at least one first shaft on the first neural probe, and separately addressing a second electrode located either on a second side of the at least one first shaft or on a surface of at least one second shaft of a second neural probe connected to the first neural probe to the measure extracellular potentials in the biological tissue.

BRIEF DESCRIPTION OF THE DRAWINGS

FIG. 3A is a top view of a device containing two 5 mm long shafts. The inset shows the recording electrode arrangement. FIG. 3B is a SEM image of the tip of a fabricated probe. The gold electrodes have an area of 100 µm$^2$, and the shafts have a thickness of 50 µm.

FIG. 5A is a photograph of a 2" diameter wafer. FIGS. 5B and 5C are front and back views of a representative finished device showing identical electrode patterns. There was an insignificant (~10 µm) misalignment between features on the two sides.

FIG. 7A show that adjacent layers have a spacing of 100 µm, which is set by the thickness of the flexible cable; some misalignment can be seen at the tips. FIG. 7B is a top view of the rear section showing the three-layer structure. FIG. 7C is a side view showing that the shafts are stress balanced and are able to retain approximately constant relative spacing.

FIG. 9B shows waveforms of 620 spikes that are assigned to a single cell.

FIGS. 10A-10C provide demonstration of single-cell recording in the rat hippocampus in one embodiment. The device in FIG. 10A was used after plating the electrodes with Pt black. FIG. 10B shows segment of data from a single channel (the fourth from the bottom on the left shaft) showing multiple spikes of different amplitudes. FIG. 10C show three waveform clusters obtained from the measurements.

FIG. 11A is a rendered image of a probe; inset: close-up of a probe tip. FIG. 11B is an image of a probe mounted onto a flexible circuit cable with anisotropic conductive film. Note that the electrical connections face the flex cable. FIG. 11C is a scanning electron microscope (SEM) close-up image of a probe tip.

FIG. 12A shows that micromachined silicon probes are stacked on top of one another with spacers comprising anisotropic conducting film (ACF), flex cables, integrated circuits, printed circuit boards (PCBs) or a combination thereof. The configuration of each layer can be customized. Although not depicted here, the dual-side polish of the thin silicon wafers enables electrodes to be patterned on both top and bottom faces of the probe. FIG. 12B shows that the individual pieces are bonded together via a thermal bonding process. FIG. 12C shows a close-up of a conceptual 4×4 shaft 3D probe assembly; each probe can offer dual-side recording capability.

FIGS. 13A-13B show side views of micromachined probes built from a thin silicon substrate. The dashed line represents the axis separating the top and bottom half of the substrate. FIG. 13A illustrates a dual-side probe with identical electrodes patterned on both front and back sides of the substrate. FIG. 13B illustrates a probe containing recording sites on one side, and microfluidic vias on the other. Such a configuration can be useful for recording brain activity during local delivery of drugs such as neurotransmitters or ion channel blockers.

FIG. 14A is a SEM image showing the interconnects are 200 nm wide, 70 nm thick, and have a center-to-center spacing of 200 nm. FIG. 14B is a SEM image showing that the electrical connections on front end of the probe are defined via electron-beam lithography. It should be noted that other lithography techniques, such as UV lithography, can also be used. FIG. 14C is a SEM image showing that the probe contains 64 electrodes arranged in a linear configuration. The last electrode, which is larger than the rest, serves as a reference. The use of e-beam lithography over conventional fabrication techniques allows denser recording of neuronal activity with reduced probe cross-sectional area. Such an approach could be combined. FIG. 14D is an optical image showing that the back end (wide part) of the probe is fabricated using standard photolithography techniques.

FIGS. 15A-15C show dual-side microelectrode arrays fabricated on 50 μm thick silicon shafts. FIG. 15A is an optical image showing the front view of the device. The shaft dimensions are 4 mm×70 μm×50 μm. Sealing epoxy is visible at the base of the structure. FIG. 15B provides optical images showing expanded view of the front and back side (left and right images, respectively). The recording sites are gold plated and have a geometric area of 100 μm$^2$. FIG. 15C shows a schematic of integrating the device with flexible circuit boards; one board for each side of the array. Electrical connections are made via low profile flip-chip bonds.

FIGS. 16A-16C show multisite recordings of spiking activity in the locust antennal lobe at a dual-side microelectrode array. FIG. 16A shows segments from 4 simultaneously recorded channels located on the same array. Signals are sampled at 15 kHz, and filtered from 300 to 5000 Hz. Spikes are visible on 3 of the 4 channels. FIG. 16B shows superimposed spike waveforms from a putative projection neuron. Note that the spike is captured on multiple channels. The solid black lines represent the averaged waveform. FIG. 16C is a raster plot of two single units that are recorded in parallel. Five consecutive trials are shown for each cell. The gray bar indicates a 1 second apple odor presentation to the antenna.

FIGS. 19A-19C show a stack of 2 silicon devices that is used to create a 3D multilayer structure. FIG. 19A is an optical image showing a 2×2 shaft arrangement. FIG. 19B is an optical image showing an expanded view of the tip. FIG. 19C provides a schematic of connecting the inner facing electrodes to a flexible circuit board spacer.

FIG. 20 shows the double-layer array probe that measures the extracellular potential of a single projection neuron in 3D. The waveforms, representing the average of 786 spikes, are placed next to their corresponding recording sites. A graphical representation of the device is used showing 16 functional electrodes. For clarity the top left shaft is omitted from the diagram. Note that all sites face inward and therefore sample the same volume.

FIG. 22A is a graphical representation of the top (i) and 3D (ii) cross sectional views of the basic structural component of an 8×8 shaft array. Shafts have width and thickness w, and nearest neighbor spacing d. The shaded hemispheres, radius r, represent the approximate detection volume surrounding each electrode.

Arrays containing multiple modular components would have vertical electrode spacing of $2r$. FIG. 22B illustrates that the detection radius as a function of total system noise is plotted for three characteristic decay lengths. FIGS. 22C and 22D represent the fractional detection volume and fractional displacement volume as a function of shaft spacing. FIG. 22C uses the assumption w=25 μm.

DETAILED DESCRIPTION OF THE PREFERRED EMBODIMENTS

One embodiment provides a new architecture for implantable microelectrode arrays for in vivo recording and stimulation of neural activity in the brain. The array contains one or more neural probes to measure extracellular potentials in a biological tissue, such as brain tissue, for example to measure electrical multineuronal activity in the brain with single cell and spike time precision. An example of a neural probe is a device that is implanted beneath the surface of the brain, and collects electrical signals arising from local neurophysiological activity, such as action potentials and local field potentials. The array comprises one or more of the following features: (i) the substrate comprises thin (<150 μm) silicon wafers; the probe is fabricated by etching the wafer all the way through its thickness, and no backside wafer thinning process is used; (ii) the dual-side polished surface of the wafers allows either electrodes to be patterned on both sides or electrodes on one side and microfluidic vias for local drug delivery on the other; (iii) the probes can be stacked on top of one another with a spacer to produce a modular three-dimensional recording array; the spacer material can be flexible or rigid printed circuit board and/or anisotropic conductive film. This allows electrical connections to be made via a thermal bonding ("flip-chip bonding") process, which is used in lieu of the conventional wire bonding method commonly used to connect conventional silicon probes onto printed circuit boards; (iv) the electrode size, spacing, and position can be customized in three dimensions; (v) to maximize the electrode density without sacrificing too large a probe volume, electron-beam lithography may be used to define electrical circuitry at the front of the probe, allowing up to about a five-fold reduction in probe width relative to conventional processing techniques (i.e. UV photolithography).

Probe Fabrication
Silicon Wafer Handling

Figure 1:
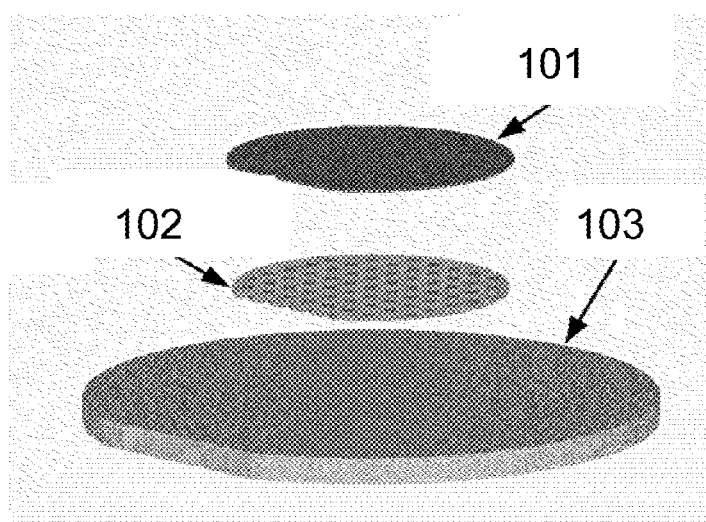
FIG. 1 shows the structure of the carrier-assisted-wafer scheme for handling ultra-thin silicon substrates.

Any suitable substrate can be used for the probes, including a semiconductor wafer, such as silicon. Other substrates, including for example metal, glass, ceramic, polymer, can also be used. In most embodiments, to facilitate handling, the ultra-thin silicon wafers can be temporarily bonded to a silicon or quartz carrier by means of a polymeric adhesive (WaferGrip, Dynatex), and de-bonded with a solvent (StripAid, Dynatex) heated to 140° C., and subsequent rinse in acetone and isopropanol. Other carriers, including ceramic, metal, glass, or polymer can also be used. The carrier is preferably thicker than 150 microns thick. Bare ultra-thin wafers can be air dried. FIG. 1 illustrates the temporary bonding stack structure. The polymeric adhesive 102 can be placed between a carrier substrate 103 and an ultra-thin substrate 101. An ultra thin substrate can have a thickness of, for example, less than about 150 microns, such as about 25 to about 50 microns. In certain steps, the wafer can be appreciably bowed under asymmetric stress; accordingly, a weight, such as a 200 gram mass, can be placed on top of the stack to ensure a flat profile. The stack can then be placed in a room temperature vacuum oven that is allowed to reach 110° C. for 30 minutes, and then be cooled back to room temperature. The long thermal cycling time can ensure that the ultra-thin wafer can be uniformly adhered to the carrier, allowing the stack to be ready for processing.

An alternative temporary bonding strategy can involve a thin layer of spun-on photoresist as an adhesive. In one embodiment, this approach is only employed at the final, deep reactive ion etch (DRIE) step, where the other polymer does not appear to provide sufficient thermal anchoring to the carrier substrate.

Single-sided Device Process

Advances in MEMS fabrication technology, particularly in DRIE have led to the use of ultra-thin silicon over other substrates of comparable thickness. The silicon can have two smoothly polished surfaces, which are both amenable to microprocessing and flip-chip bonding.

Figure 2:
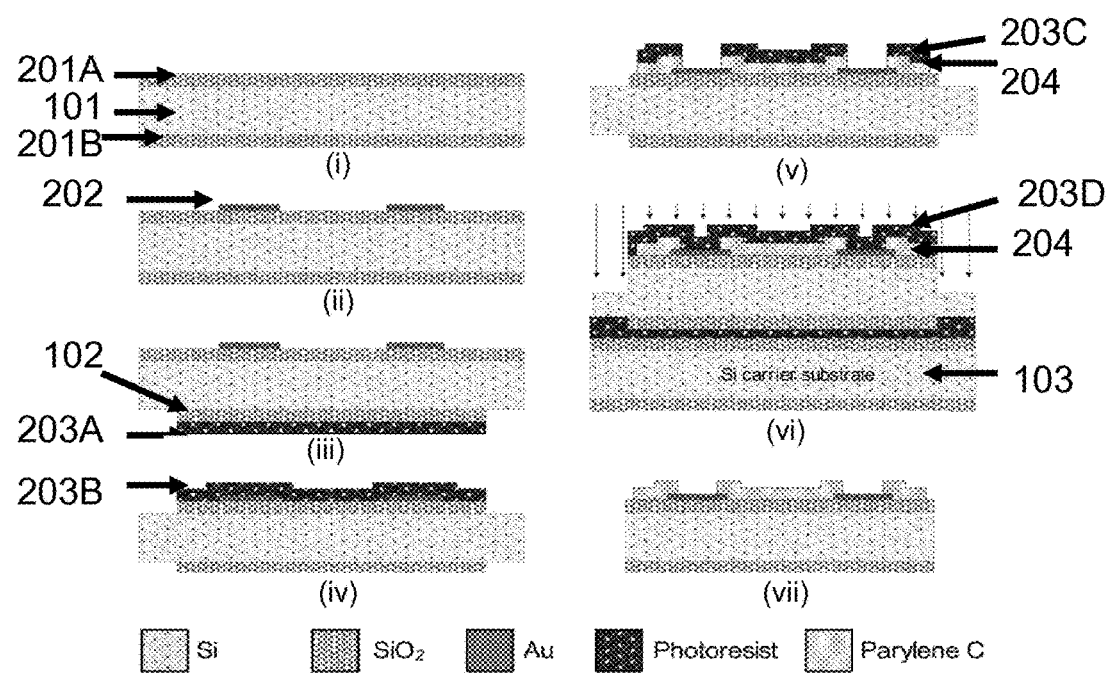
FIG. 2 provides a fabrication process flow chart for single-sided neural probe built from ultra-thin silicon substrates. In this embodiment, each step relies on the use of a rigid supporting wafer to maintain structural integrity of the substrate.

The neural recording arrays can be manufactured using surface and bulk micromachining technologies; an example is illustrated in FIG. 2. The starting material can be a silicon substrate 101, such as a double-side polished ultra-thin Si (100) substrate. Substrate thickness may be, for example, less than about 150 μm, such as less than about 100 μm, such as less than 50 μm, such as less than 25 μm. Other semiconductor (e.g., gallium arsenide or silicon carbide) or non-semiconductor (e.g., glass, organic polymer, such as parylene, diamond, plastic, ceramic) substrate can also be used. In one embodiment, the thickness is between about 25 and about 50 μm. The substrates can be first thermally oxidized to yield a oxide layer 201A, 201B on both sides, as shown in step (i). The oxide layer can be, for example, less than 5 μm thick, such as 2 μm thick. Other insulating layers may also be used. In step (ii), recording electrodes 202 are formed by lift off on the oxide layer 201A. The metallization can be carried out, for example, in a thermal evaporator and comprise a 30 Å of chromium adhesion layer followed by 1500 Å of gold. Any suitable metals, such as noble metals, can be used. The noble metal can include, platinum, gold, iridium, or a combination thereof. The substrate can then be ultrasonicated in acetone to lift off the unpatterned metal and photoresist, leaving behind the finished electrode patterns. The electrodes 202 can be separately addressable. A separately addressable electrode means that a read circuit can read the electric signals (e.g., current) from an individual electrode.

In step (iii), as back side oxide layer 201B is masked by forming a photoresist mask 203A, and patterning the oxide layer. In step (iv), the front side oxide layer 201A is patterned by RIE using photoresist layer 203B as a mask. In step (v), a film of insulating material, such as a polymer film, such as parylene, 204 is deposited over electrodes 202. Layer 204 is patterned by RIE, using photoresist layer 203C as a mask to form openings exposing electrodes 202. The layer 204 can be deposited and patterned with oxygen plasma (see Pang et al., "A new multi-site probe array with monolithically integrated parylene flexible cable for neural prostheses," *27th Annual International Conference of the IEEE Engineering in Medicine and Biology Society*, 2005, pp. 7114-7117). The insulating layers are defined, and the electrode recording sites are exposed. For the DRIE step, the ultra-thin wafer 101 can be transferred to a carrier 103 containing photoresist as the adhesive. A photoresist layer 203D with a thickness of less than about 50 μm, such as 20 μm, can be spun on and patterned into a masking layer, which is followed by DRIE through the exposed area in step (vi) to form the base and one or more shafts of the probe. At this stage, the probes can be fully defined, and after releasing them from carrier 103 in acetone and rinsing in isopropanol and ethanol, the device is ready for use.

Figure 3A:
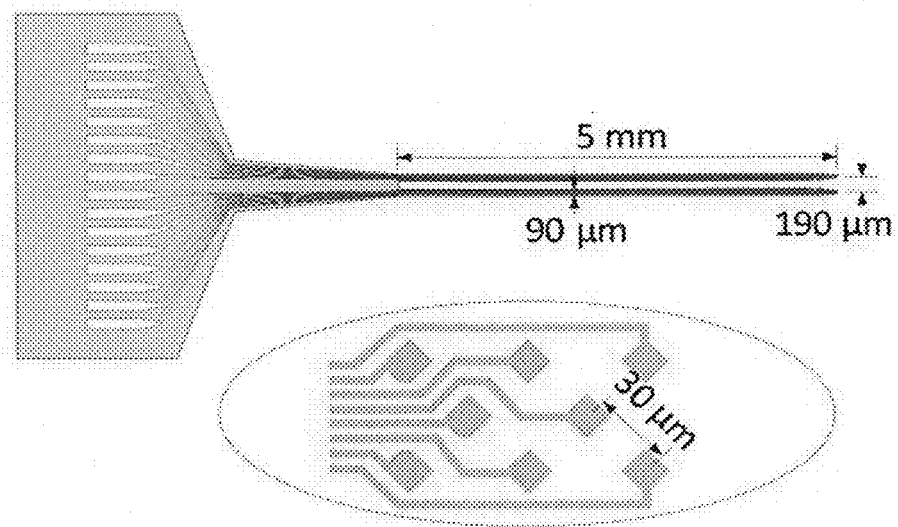
FIGS. 3A-3B show the structure of a neural probe.
Figure 3B:
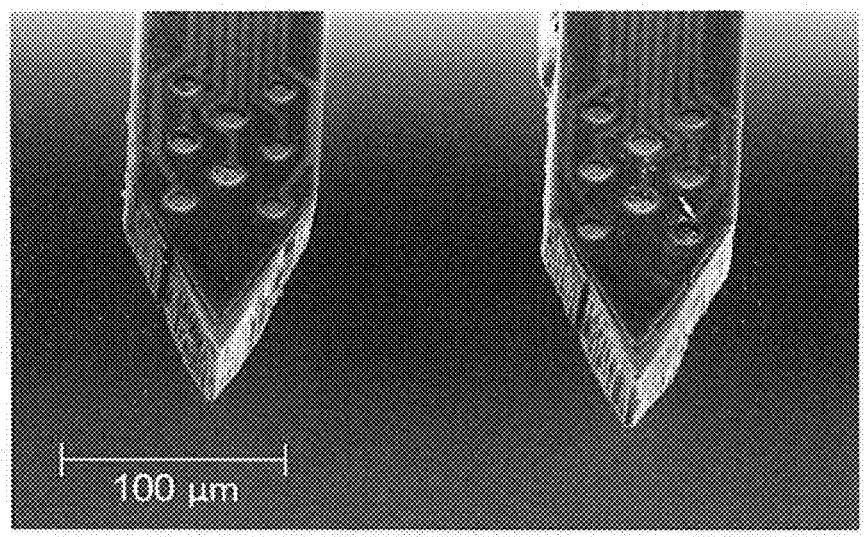
Figure 4:
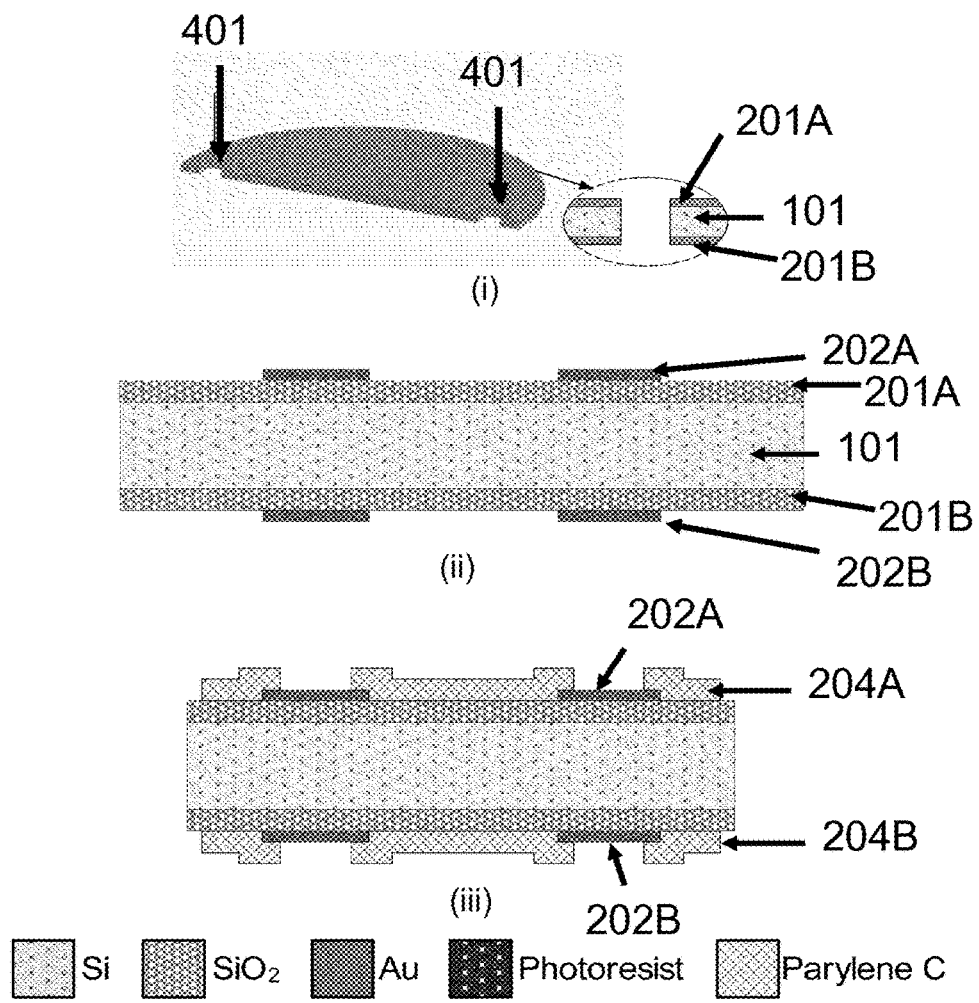
FIG. 4 provides a modified process flow chart for fabricating dual-side probes on ultra-thin silicon substrates. The etching of through-holes is important for achieving precise back side feature alignment. After metal has been evaporated on both sides, identical parylene and oxide etch steps are carried out on each side before the final DRIE step.
Figure 11A:
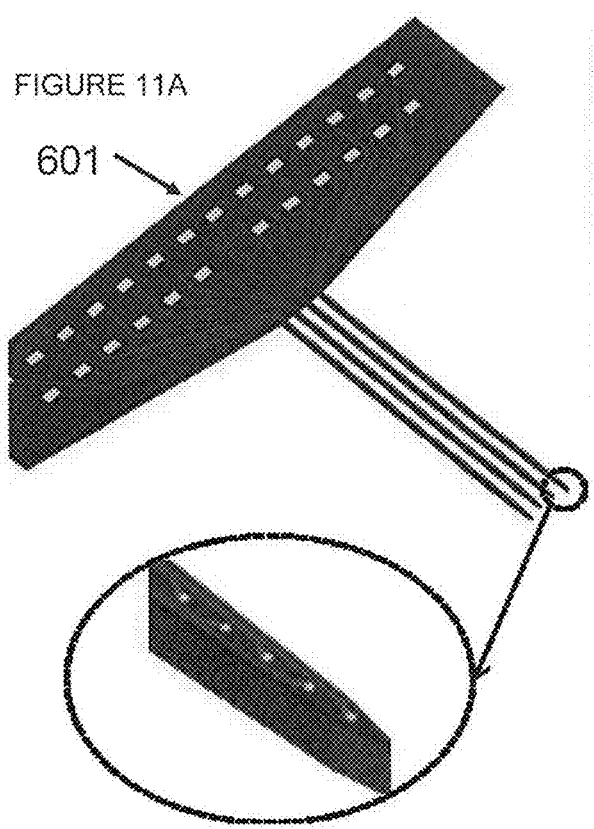
FIGS. 11A-11C show micromachined silicon neural probes fabricated from ultrathin silicon substrates.
Figure 11B:
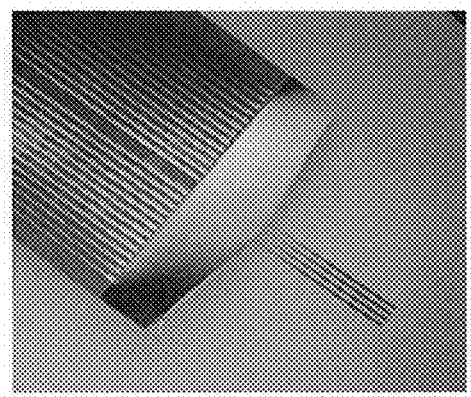
Figure 11C:
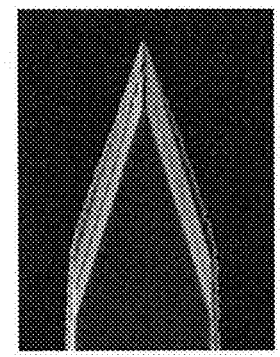
Figure 14A:
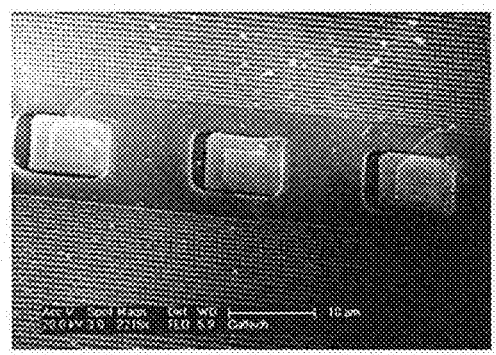
FIGS. 14A-14D show a neural probe employing nanofabricated metallic interconnects.
Figure 14B:
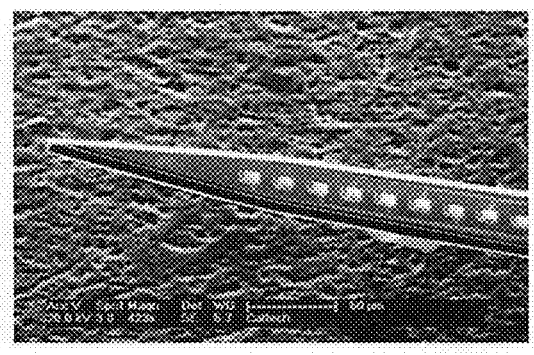
Figure 14C:
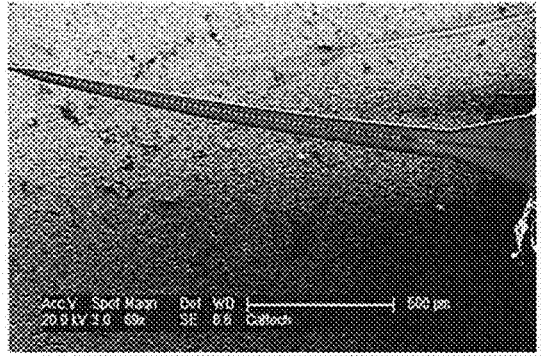
Figure 14D:
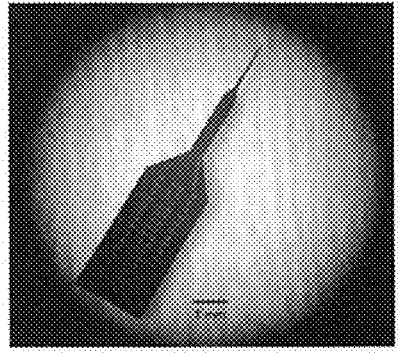

A representative fabricated device is shown in FIG. 3A, with an expanded SEM view of the tip in FIG. 3B. The number of the electrodes disposed on a shaft can be of any number that is suitable. For example, it can be at least 2, such as at least 4, such as at least 8, such as at least 16. The electrodes can be arranged in any desirable pattern, depending on the specific use. For example, FIGS. 14A-14C show the nanofabricated metallic interconnect electrodes in one pattern on a shaft, whereas FIG. 3B shows another pattern. The electrodes 202 can be on both the front and back sides of a shaft portion of substrate 101 as described in FIG. 4. Multiple shafts can be extended from a base. For example, as shown in FIGS. 11A-11C, four shafts are extended from a base. The number of shafts can be any suitable number, including for example at least 2, at least 4, at least 8. An exemplary rendered image of a probe with 4 shafts 601 is provided in FIGS. 11A and 11B.

Dual-Side Device Process

Double-sided electrode configurations have previously been realized with a different technique involving through-holes (Perlin et al., "The effect of the substrate on the extracellular neural activity recorded with micromachined silicon microprobes," 26th *Annual International Conference of the IEEE Engineering in Medicine and Biology Society*, 2004, pp. 2002-2005, vol. 3), but the approach described herein can offer an advantage of separately addressable sites on the front and back sides of a shaft. For reference, the back corresponds to the surface that undergoes the second metallization step, and the front corresponds to the exposed surface during DRIE, but the two terms can be reversed. Not to be bound by any particular theory, but this design can provide electrical localization of neuronal signals (for better isolation of multiple units) and mechanical robustness of the shafts (more fault-tolerant due to the absence of through-holes, which may weaken the structure). Development of dual-side probes based on flexible polyimide substrates is known in the art (see e.g., Stieglitz et al., "Flexible BIOMEMS with electrode arrangements on front and back side as key component in neural prostheses and biohybrid systems," *Sensors and Actuators B*, 2002, pp. 8-14, vol. 83).

One challenge in processing both sides of the wafer can be the acquisition of precise feature alignment between the front and back sides. Although many UV mask aligners provide the option of back-side alignment, this approach is found to produce as much as 40 µm feature misalignment. To overcome this difficulty, the approach employed in one embodiment is to define etched through hole alignment marks 401, via DRIE through the ultra-thin wafer 101, at the onset of the fabrication process (see FIG. 4, step (i)) to minimize substantially the need for imaging through the carrier substrate. The wafer can comprise oxide layer(s) 201A, 201B as described above.

Figure 5A:
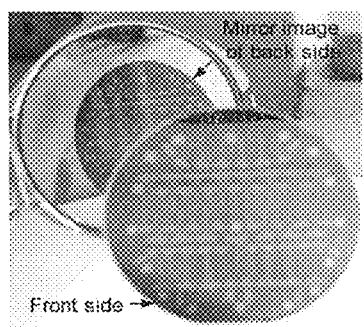
FIGS. 5A-5C are images of dual-side features on ultra-thin Si substrates.
Figure 5B:
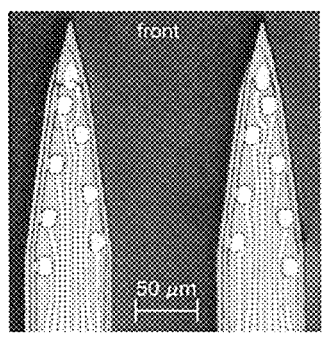
Figure 5C:
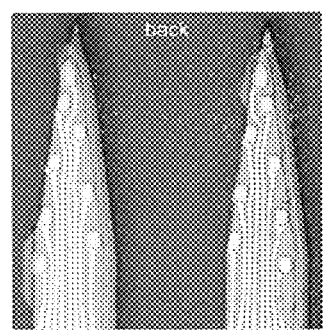

The next two steps in the process sequence involve metallization on both sides of wafer 101 using the etched alignment marks 401. Metallization, as described previously, can comprise depositing and patterning metal electrodes 202A and 202B on the front and the back side of the wafer 101 as shown in step (ii) in FIG. 4. As FIG. 5A shows, the fabrication can take place at the whole wafer level, resulting in a high-yield process. The remaining steps can proceed in the same fashion as for single-sided devices described above and can be mirrored on the back side. The wafer can be patterned to form the base(s) and shafts(s) and the probes are then be released from the carrier. The completed device is shown in step (iii). The process can yield devices with back side feature alignment equal to or better than 20 µm, such as 10 µm, such as 5 µm. A small amount of misalignment may be tolerated. FIGS. 5B and 5C depict front and back views of a dual-side device in one embodiment.

Packaging and Assembly

Figure 6:
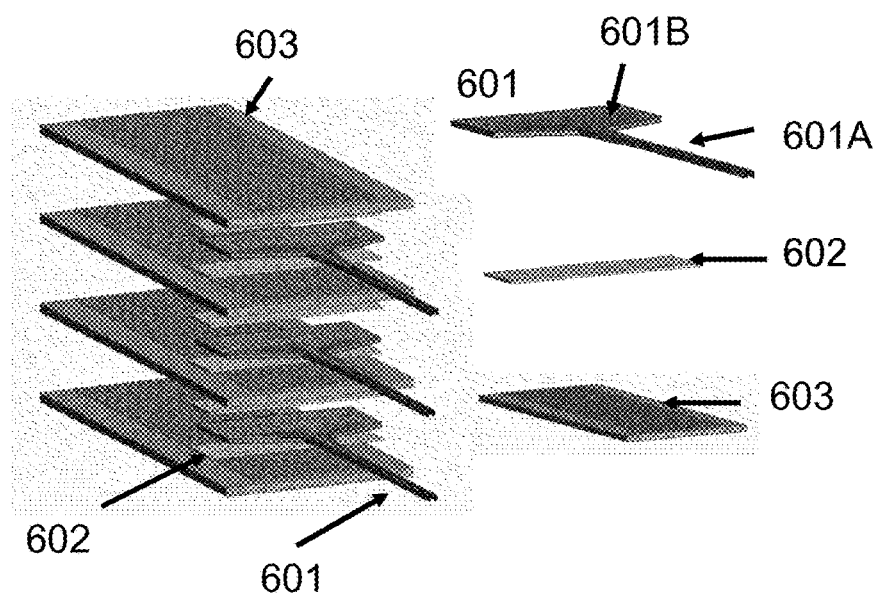
FIG. 6 shows a flip-chip assembly scheme for bonding the silicon devices to flexible cables. The z-axis anisotropic conductive film permits current to flow out of plane between the device and flexible cable, but remains highly resistive in plane. The assembly can be repeated several times to produce 3D structures.

The finished silicon devices are flip-chip bonded to custom built flexible polyimide cables, or other read out devices such as printed circuit boards, which transfers signals to off-chip active electronics. Flip-chip bonding is generally known in the art. Flip-chip bonded connections can have a low, flat footprint, which can enable multiple layers of silicon chips and printed circuit boards to be stacked together to create a three-dimensional (3D) structure. Moreover, the flat footprint allows flip-chip bonding to be carried out on both sides of the silicon chip. The modular assembly architecture is represented in FIGS. 6 and 12A-12C. The left side of FIG. 6 shows the 3D structure and the right side shows components of the 3D structure.

Figure 12A:
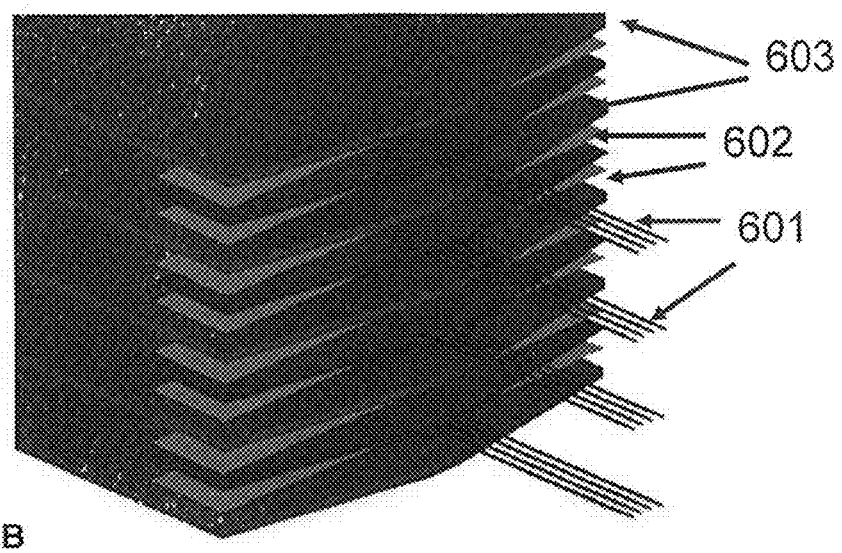
FIGS. 12A-12C provide rendered images of a 3D neural probe, assembled from 2D parts.
Figure 12B:
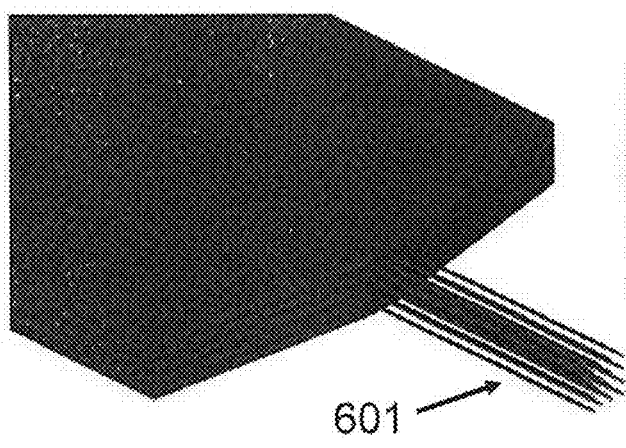
Figure 12C:
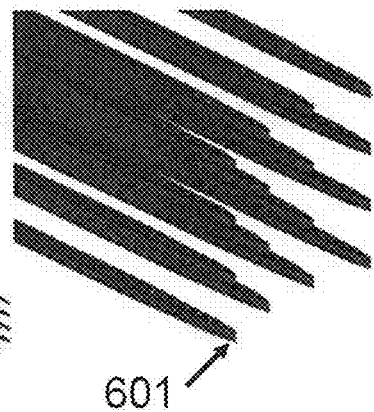

As shown in FIGS. 6 and 12A, the silicon probes 601 containing shafts 601A and base 601B can be stacked on top of one another with spacers comprising z-axis anisotropic conducting film 602, which upon curing the film with heat and pressure, permits current to flow out of plane but can remain highly resistive in plane. The spacer can comprise a rigid or flexible material. The flexible cable 603 can contain metallic leads on each side, thereby providing separate electrical access to electrodes 202A and 202B on the front and back of adjacent silicon probes. One advantage of this approach is the ability to deploy recording sites that sample the same volume from opposite directions, with a customizable separation determined by the flexible cable thickness. The thickness can be of any suitable value, such as less than 200 µm, such as 100 µm in one embodiment. This can provide up to a two-fold gain in the volume sampled between adjacent silicon layers and can augment the 3D localization of neuronal membrane currents.

Figure 7A:
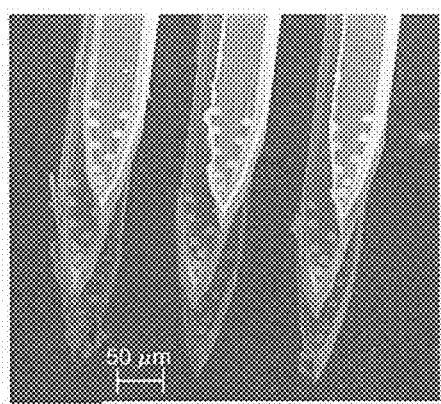
FIGS. 7A-7C show a 3×3 shaft array produced by 3D flip-chip assembly. This device contains 144 electrodes in a ~0.02 mm$^3$ rectangular volume (electrodes on the back side are not visible in the images).
Figure 7B:
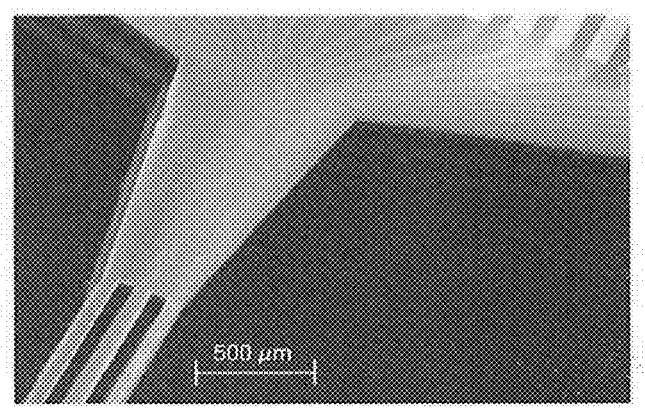

Following assembly, the contact region can be encapsulated in electronic-grade epoxy. FIG. 7A displays the tip of an exemplary 3×3 shaft array, containing a total of 144 recording sites (8 electrodes per shaft×2 sides), showing the ability to assemble 3D neural probes combining dual-side electrode arrays with multilayer structures. In a 3D multilayer structure, such as the one shown in FIGS. 6 and 12A-12C, the bases 601B of different probes can be bonded to one another. Any type of suitable bonding, such as thermal or flip-chip bonding, can be used. The electrodes can be disposed on the front and/or back sides of the shaft 601A. In the embodiment shown in FIGS. 7A-7B, the layers are aligned manually with the aid of a low power magnification stereo microscope. Alternatively, they can be aligned with more advanced flip-chip bonding tools to provide better alignment results.

Figure 7C:
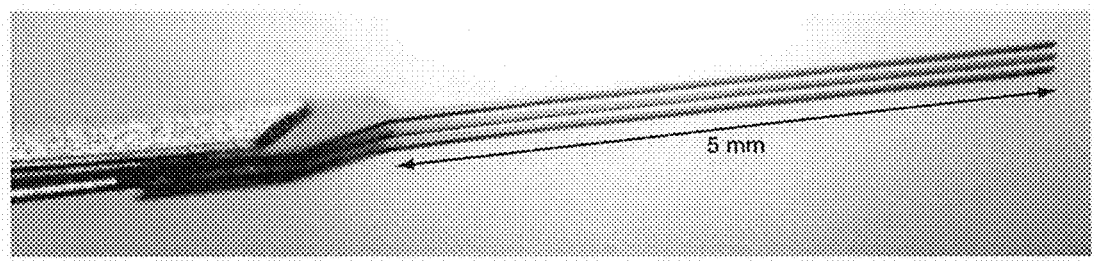

The probes, particularly the shafts thereof, can be stress balanced by the presence of identical features on both sides, thus allowing adjacent layers in the 3D stack to retain a constant relative spacing. The balance of stress can be important for maintaining straight shafts targeted at deep brain regions. The length of the shafts can be of any desirable length. In one embodiment, as shown in FIG. 7C, the shafts are between 1 and 10 mm, such as 5 mm long and have a cross section of 10-100 µm ×15-75 µm, such as 70 µm×50µm, and the substantially constant relative spacing can be obtained with the shafts being stress balanced. The spacing can be less than about 400 microns, such as less than 300 microns, such as less than 200 microns, such as less than 100 microns, such as less than about 50 microns. Also, in the embodiment multiple players of probes are present, the length of the probes in different layers, or within the same layer, can be the same or different from one another. The electrode and shaft spacing can be adjusted to increase the sampling density and sampling volume. The electrodes in the 3D structure can then detect electric signals from the sampling volume of the tissue, thus providing information about the tissue in 3D. In another embodiment shown in FIG. 13B, wherein the electrodes 202 are disposed on one side of the shaft 101/601A. An etched via 701 is provided through insulating layer 204 for electrode access 701. This side is used for electrophysiological recording. The other side of the shaft can serve as a substrate for microfluidic vias 702, which deliver drugs to select locations along the probe shaft. FIG. 13A shows the tip of shaft 601A containing electrodes 202A, 202B on both sides of the substrate 101 of shaft. Vias 701 are provided through insulating layers 204 to access the electrodes 202A, 202A.

3D Recordings

The results described herein establish the feasibility of achieving dense extracellular measurements with three geometric degrees of freedom and the potential to scale up the devices described herein to a large scale recording application. A slightly lower sampling density and larger volume may be ideal for interrogating substantial fractions of discrete structural units of neuronal ensembles, such as cortical columns, with the goal of providing further insight on columnar organization and its computational role in the cortex (Mountcastle, V. B., "The columnar organization of the neocortex," *Brain*, 1997, pp. 701-722, vol. 120). Such devices could also be used to map extracellular current source densities in 3D, in order to characterize information flow within and between multiple structures (Bragin et al., "Gamma (40-100 Hz) oscillation in the hippocampus of the behaving rat," *J Neurosci*, 1995, pp. 47-60, vol. 15). Finally, large, coarse scale studies may be the most appropriate for functional mapping of $mm^3$ level volumes, such as 10 $mm^3$, containing close to ~$10^5$ neurons such as ~$10^4$-$10^5$ neurons, and may present a useful complement to functional magnetic resonance imaging, whose spatial resolution is limited to ~1 $mm^3$ and temporal resolution does not enable single-spike detection (Logothetis et al., Neurophysiological investigation of the basis of the fMRI signal," Nature, 2001, pp. 150-157, vol. 412). They may also hold promise as an alternative method to voltage sensitive dye imaging (Mann et al., "Perisomatic feedback inhibition underlies cholinergically induced fast oscillations in the rat hippocampus in vitro," *Neuron*, 2005, pp. 105-117, vol. 45), by enabling access to regions deep inside the brain without the need for using slices.

Figure 22A:
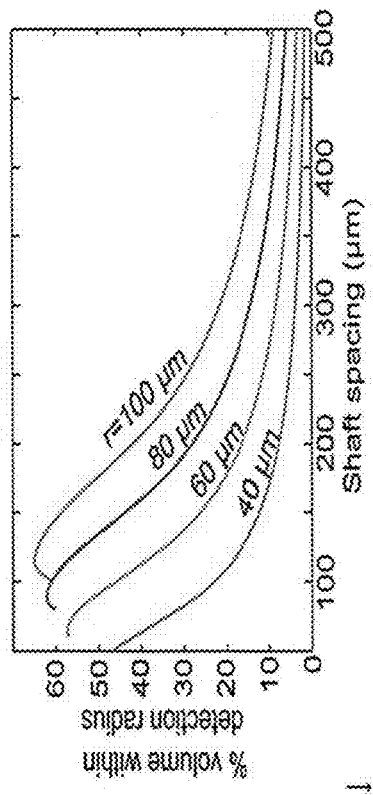
FIGS. 22A-22D illustrate the limitation of 3D extracellular recordings in one embodiment.

A coarse scale recording device would maximize the volume probed with minimal use of recording sites. Applications demanding higher spatial resolution measurements and better single-unit isolation reliability would require packing a larger number of recording sites per unit length of the shaft, at the cost of more data channels. FIG. 22A represents a cross section of the basic structural component of a proposed large scale 3D microelectrode array. The device has 8×8 shafts and exploits both the dual-side and multilayer device attributes. The width and thickness of the shafts are assumed to be the same (w), and the nearest neighbor spacing (d) is equal along the vertical and horizontal axes. The detection volumes surrounding the electrodes are approximated as hemispheres of radius r, which is defined as the maximum distance that an electrode can pick up action potentials. Each shaft contains only one recording site on the front as well as the back side of each shaft, and is therefore suited for moderate to coarse spatial scale measurement applications. In order to increase the depth of tissue probed by the 3D structure, the unit module (length 2r) can be replicated along the longitudinal axis of the shafts. However, since all components are substantially identical, it is sufficient to consider a single module in the treatment that follows.

Alternative 3D structures may be fabricated. As an example, an 8×8 shaft device, in which the structural dimensions are reduced to w=25 μm (Najafi et al., "Scaling limitations of silicon multichannel recording probes," *IEEE Trans. Biomed. Eng.*, 1990, pp. 1-11, vol. 37) through the use of nanofabrication techniques, is used. A spacing of d=200 μm would displace 2% of the structure's volume, which appears to be an acceptable value for some systems (Campbell et al., "A silicon-based, three-dimensional neural interface: manufacturing processes for an intracortical electrode array," *IEEE Trans. Biomed. Eng.*, 1991. pp. 758-768, vol. 38.). Assuming r=100 μm, a 1 mm-long device would require 5 modular components (since each module is 200 μm long), bringing the total number of data channels to 640. About 40% of the 1.8×1.8×1 $mm^3$ enclosed volume would lie within the detection radius of an electrode. Based on previous investigations, one typically detects only 1 to 10% of total available neurons in a selected region (Shoham et al., "How silent is the brain: is there a dark matter problem in neuroscience?" *J. Comp. Physiol. A.*, 2006, pp. 777-784, vol. 192). Hence given a neuronal density of 50,000 per $mm^3$, between 650 and 6,500 units in 3.2 $mm^3$ of cortex can be measured.

Ultimate Limitations of 3D Extracellular Recordings

As the scale and complexity of the implanted structure increases, the risk of disrupting physiological brain activity is likely to rise. This suggests that the amount of tissue damaged by the silicon microstructure, and the volume accessible for measurement are two fundamental system design constraints. The former constraint requires small shafts and large shaft spacing, while the latter requires a large SNR and densely packed electrodes.

Noise in extracellular recordings can arise from three sources: (i) the amplifier electronics and external electromagnetic interference, (ii) noise at the electrode-fluid interface, and (iii) unsorted low amplitude brain activity. The combination of these processes will be manifested as the total measured noise that determines the SNR, and is given by:

$$\delta V_{tot}^2 = \delta V_{amp}^2 + \delta V_{electrode}^2 + \delta V_{brain}^2 \qquad (1)$$

Combining equation 1 with equation 2 provided below can allow estimation of the detection radius. A minimum SNR of 3 can be assumed desirable to detect a spike. FIG. 22B displays r as a function of total measured noise, for three different characteristic decay constants. The total root mean squared (RMS) noise in the working examples was found to be 16.5 μV in the 300 to 5000 Hz band that is suitable for spike detection. The corresponding detection radius assuming λ=22 μm is estimated to be 46 μm.

In order to improve the recording yield by increasing r, strategies to minimize noise were explored. By performing separate tests with the amplifier as well as the electrodes immersed in locust saline, it was determined that $\delta V_{amp}$=13 μV, $\delta V_{electrode}$=6.6 μV, and by process of elimination, $\delta V_{brain}$=7.7 μV, with about 1 μV standard deviation across channels. Electrophysiological amplifiers with $\delta V_{amp}$=2 μV have been demonstrated (Harrison et al., "A low-power low-noise CMOS amplifier for neural recording applications," *IEEE J Solid-State Circ*, 2003, pp. 958-965, vol.

383). Furthermore, the observed electrode noise was consistent with a predominantly thermal noise mechanism from the real component of the impedance. Because impedance is inversely proportional to surface area, if area were scaled up from 100 to 400 µm² this would translate to $\delta V_{electrode} \approx 3$ µV. It is predicted that the larger area would have a negligible impact on extracellular action potential amplitude (Moffitt et al., "Model-based analysis of cortical recording with silicon microelectrodes," *Clinical Neurophysiol.*, 2005, pp. 2240-2250. vol. 116). Hence, the lowest projected noise would be dominated by biological processes and would equal about 8.5 µV, which corresponds to a maximum measurement range of 100 µm, assuming λ=22 µm.

The estimate of r in the locust antennal lobe was in close agreement with an estimate obtained by a different method using multisite probe measurements of neurons in the rat hippocampus (Henze et al., "Intracellular features predicted by extracellular recordings in the hippocampus in vivo," *J Neurophysiol*, 2000, pp. 390-400, vol. 84), as well the salamander retina (Segev et al., "Recording spikes from a large fraction of the ganglion cells in a retinal patch," *Nature Neurosci*, 2004, pp. 1155-1162, vol. 7; Shoham et al., "How silent is the brain: is there a dark matter problem in neuroscience?" *J. Comp. Physiol. A.*, 2006, pp. 777-784, vol. 1926). However, it was noted that throughout different areas of the cat cortex, $\delta V_{brain}$ has been found to vary by about a factor of 4 (Buchwald et al., J. S. and Grover, F. S., "Amplitudes of background fast activity characteristic of specific brain sites," *J Neurophysiol*, 1970, pp. 148-159, vol. 33), signifying the recording yield can be highly region specific.

Figure 22C:
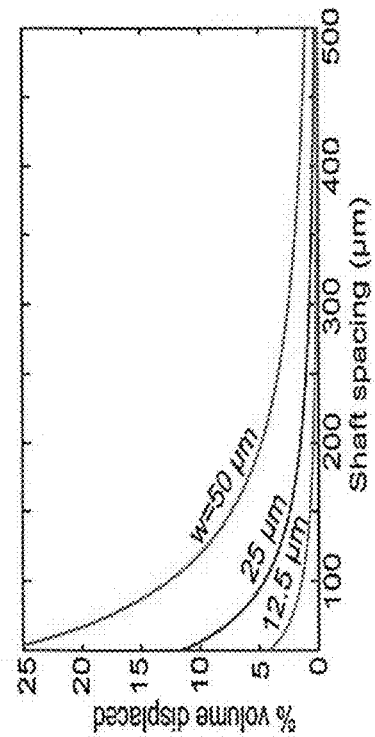
Figure 22B:
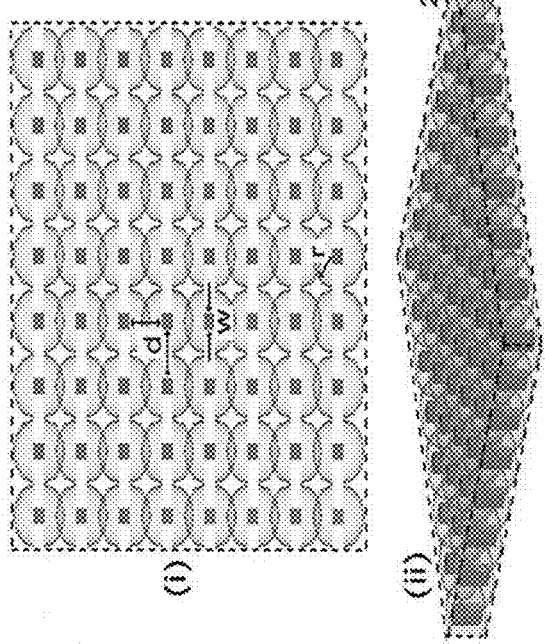
Figure 22D:
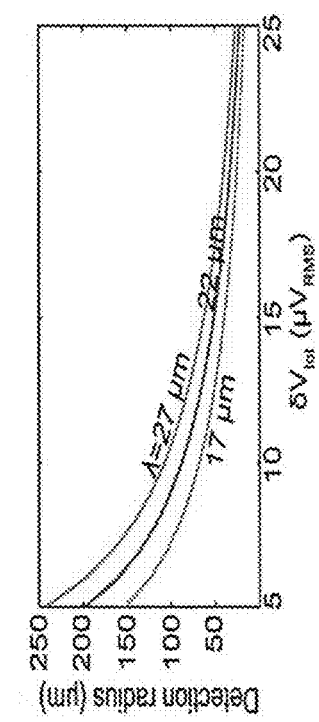

Equipped with an estimate on the upper bound of r, as shown in FIG. 22C, the unique (i.e., non-overlapping) fractional volume in the entire array that should lie within range of detection was predicted. The total cuboidal volume enclosing the structural module is defined by the dashed lines in FIG. 22A. The fractional recording volume increases with smaller shaft separation until the condition d≤r is satisfied, at which point significant overlap occurs between adjacent patches. FIG. 22D shows the percentage of tissue displaced by the implant as a function of shaft spacing. The actual level of functional disruption may be considerably more complex than what is described by a simple volumetric estimate; however, the fractional displacement volume provides a lower bound on the proportion of damaged cells expected to occur in the implanted region. FIG. 22C suggests that for a variety of r, the spacing is preferably less than about 400 microns, such as less than 300 microns, such as less than 200 microns, such as less than 100 microns.

NON-LIMITING WORKING EXAMPLES

Example 1

Single-Sided Device Process

In some embodiments of this working example, the silicon wafers underwent the handling process as described previously with respect to FIG. 2. The starting material was a double-side polished 2 inch diameter ultra-thin Si (100) substrate with a thickness ranging from 25 µm to 50 µm (Virginia Semiconductor). The substrate was thermally oxidized to yield a oxide layer on both sides. Next, a negative tone photoresist was spun on and patterned to define the recording electrodes, interconnects, and flip-chip contact pads. The metallization was carried out in a thermal evaporator and comprises a 30 Å Cr adhesion layer and a 1500 Å Au layer. The substrate was then ultrasonicated in acetone to lift off the unpatterned metal and photoresist, leaving behind the finished electrode patterns. At this point, the wafer was flipped over, remounted on a temporary carrier, and the oxide was selectively removed on the back side using a photoresist mask. The wafer was flipped over again and an RIE step was applied to remove the oxide layer on the front side, forming a shaft-like structure. A film of parylene C (e.g., 2 µm) was conformally deposited and patterned with oxygen plasma (see Pang et al., "A new multi-site probe array with monolithically integrated parylene flexible cable for neural prostheses," *27th Annual International Conference of the IEEE Engineering in Medicine and Biology Society*, 2005, pp. 7114-7117). The insulation layers were defined, and the Au recording sites (or electrodes) were exposed.

For the DRIE step, the ultra-thin wafer was transferred to a new carrier containing photoresist as the adhesive. A 20 µm photoresist film was spun on and patterned into a masking layer, which was followed by DRIE through the exposed area. At this stage, the probes were fully defined, and after releasing them in acetone and rinsing in isopropanol and ethanol, they were ready for assembly and testing. A representative fabricated device is shown in FIG. 3A, with an expanded SEM view of the tip in FIG. 3B. In the embodiment illustrated in FIGS. 3A-3B, 16 recording sites are distributed on 2 shafts, which have dimensions of 5 mm×90 µm×50 µm (l×w×t), and center-to-center spacing of 190 µm. The electrode spacing is 30 µm center-to-center.

Assembly

The finished silicon devices 601 were flip-chip bonded to custom built flexible polyimide cables, which transferred the signals to off-chip active electronics. The modular assembly architecture is represented in FIG. 6. The bonds were formed with an anisotropic conductive film (3M); upon curing the film with heat and pressure, it permitted current to flow out of plane but can remain highly resistive in plane. Following assembly, the contact region was encapsulated in electronic-grade epoxy. FIG. 7A displays the tip of a 3×3 shaft array containing a total of 144 recording sites (8 electrodes per shaft×2 sides), which demonstrates the ability to assemble 3D neural probes combining dual-side electrode arrays with multilayer structures. The image also shows a small and insignificant degree of misalignment between different layers. In the embodiment shown in FIGS. 7A-7B, the layers were aligned manually with the aid of a low power magnification stereo microscope.

The silicon shafts were stress balanced by the features on both sides, thus allowing adjacent layers in the 3D stack to retain a constant relative spacing. In one embodiment, as shown in FIG. 7C, the shafts are 5 mm long and have a cross section of 70 µm×50 µm.

Impedance Measurements

In one embodiment, the neural probes fabricated according to the processes as described before were analyzed. Two-terminal impedance measurements were performed in normal saline solution, using an off-chip Ag/AgCl reference electrode. The average impedance of the 100 µm² electrodes was found to be 2-3 MΩ (f=1 kHz) for unplated Au, in rough agreement with previously published results (Drake et al., "Performance of planar multisite microprobes in recording extracellular single-unit intracortical activity," *IEEE Trans. Biomed. Eng.*, 1988, pp. 719-732, vol. 35, no. 9). In addition, some electrodes were electroplated with Pt black (Ilic et al., "Preparation and characterization of platinum black electrodes," *J. Mat. Sci.*, 2000, pp. 3447-3457, vol. 35); this reduced impedance by 10 to 50 fold, but with highly variable results. In this example, on average about 25% of electrodes per device were defective, due to either broken leads or poor electrical contact at the flip-chip bonding site.

Acute Recordings in the Locust Antennal Lobe

Figure 8:
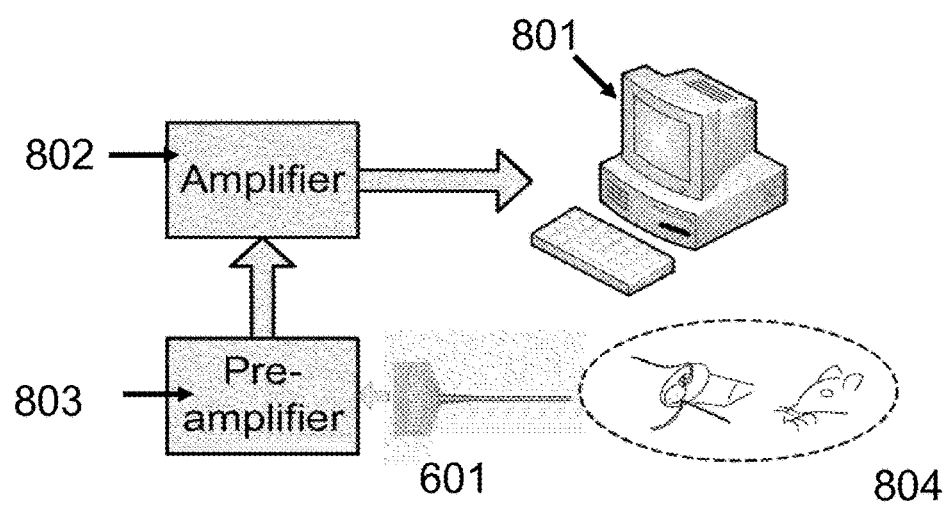
FIG. 8 provides an experimental setup for testing the probes in locusts and rats in one embodiment.
Figures 9A, 9B:
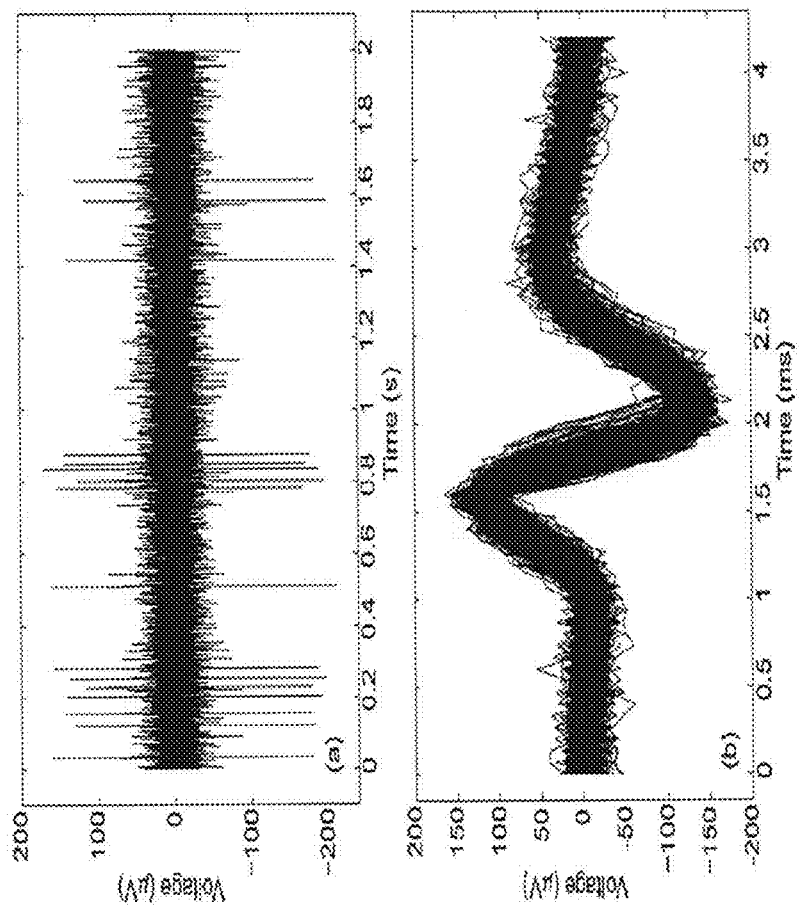
FIGS. 9A-9B show a representative segment of data from a single channel showing spikes in the locust antennal lobe (FIG. 9A) in one embodiment.

Extracellular action potentials were measured from projection neurons in the locust antennal lobe (AL) using the single-sided probe depicted in FIG. 3A-3B. The experimental setup is schematically illustrated in FIG. 8. Following insertion of the probe with a micromanipulator at a speed of ~1 μm/s, the neural tissue 804 was allowed to recover for 20 minutes before beginning the recording session. Data were sampled at 15 kHz and filtered from 0.3 kHz to 6 kHz. The electrical signals can go through a preamplifier 803, followed by an amplifier 802, before reaching a computer 801. The computer can be a general purpose computer or a specific computer chip or processor designed to run data acquisition with suitable software. A representative segment from one channel is shown in FIG. 9A, while FIG. 9B shows the superposition of 620 spike waveforms putatively ascribed to the same neuron. Activity was primarily evoked by means of an odor presentation (Laurent et al., "Encoding of olfactory information with oscillating neural assemblies," Science, 1994, pp. 1872-1875, vol. 265), but also showed spontaneous action potentials. The results demonstrate that such devices may be used for measuring extracellular action potentials.

Acute Recordings in the Rat Hippocampus

A probe with the electrode geometry shown in FIG. 10A, whose electrodes were plated with Pt black, was acutely implanted in the hippocampus of an anesthetized rat. The device comprised two shafts of dimensions 5 mm×100 μm×50 μm (l×w×t). The geometric area of the recording sites was varied in the design from 25 μm$^2$ to 1225 μm$^2$, to measure the dependence of spike amplitude on electrode area (Moffitt et al., "Model-based analysis of cortical recording with silicon microelectrodes," Clinical Neurophysiol., 2005, pp. 2240-2250. vol. 116). A clear, systematic dependence on area was not observed. The results are confounded by variations in impedance and distance from the spiking neuron, both of which can affect spike amplitude. Two additional devices were inserted; the Au coated array in FIG. 3A, as well as a Pt plated electrode array with similar cross section but smaller electrode separation (not shown).

The dura was removed prior to insertion. During device penetration, it was observed that the brain deformed under pressure from the probe. The tissue eventually relaxed after insertion, but some permanent disruption may have occurred in the region surrounding the shafts. In all cases the probe was advanced in 100 to 200 μm steps to a final depth of 3 mm, and the brain was allowed to recover for 1-5 minutes at each step. Extracellular recordings of spontaneous firing activity from three putative neurons are plotted in FIGS. 10B and 10C. Data were sampled at 25 kHz, filtered digitally from 0.3 kHz to 6 kHz, and spikes were clustered using a Matlab program modified from (Rutishauser et al., "Online detection and sorting of extracellularly recorded action potentials in human medial temporal lobe recordings, in vivo," J. Neurosci. Methods, 2006, pp. 204-224, vol. 154).

Example 2

Materials and Methods

In this example, a 50 μm thick silicon substrate was patterned on both of its polished surfaces with gold microelectrode arrays. The conducting leads were electrically isolated by a 2 μm plasma-etched parylene C layer deposited over the metal, and 2 μm underlying thermal oxide. The substrate supporting the array was shaped into two sharp shafts by DRIE through the silicon layer. A representative device assembly is shown in FIGS. 15A-15C. In this embodiment, each shaft had dimensions of 4 mm×70 μm×50 μm (l×w×t) and contained eight 100 μm$^2$ electrodes on the front as well as the back side. Shafts were spaced 80 μm apart at their widest point, and electrodes were separated by 25 to 40 μm center-to-center. In order to ensure electrical continuity of the recording sites to off-chip electronics, each structure 601 was flip-chip bonded onto a flexible printed circuit board (PCB) 603 (see FIG. 15C). A modular assembly approach was used to create the multilayer silicon device represented in FIGS. 19A-19B. Following flip-chip bonding the contact regions were sealed with epoxy. Finally, in order to improve the signal-to-noise ratio (SNR) and minimize channel crosstalk, the impedance of all electrodes was reduced from roughly 2.1 MΩ to 0.2-0.25 MΩ with electrodeposited gold. The finished devices contained 32 recording channels; 16 per side and 16 per layer for the dual-side and double-layer arrays in FIGS. 15A-15C and 19A-19C, respectively. As shown in FIG. 15C, the dual-side device comprises a separate PCB 603A for top electrodes and a separate PCB 603B for bottom electrodes, wherein the electrode are separately addressable electrodes. FIG. 19C shows two probes 601A and 601B are attached to each other at the base, separated by a PCB 603.

Single-Unit and LFP Recordings

Acute measurements were carried out with a probe as shown in FIGS. 15A-15C in locusts (Schistocerca americana), whose antennae and body were fixed, and brain desheathed and perfused with saline (Laurent et al., "Encoding of olfactory information with oscillating neural assemblies," Science, 1994, pp. 1872-1875, vol. 265). Signals were sampled at 15 kHz during five to ten consecutive 20 second trials, in which a 1 second cis-3-hexanol or apple odor pulse was applied to the antenna. Single-unit measurements were made with devices inserted in the antennal lobe, which contained excitatory projection neurons that were known to respond to odor stimuli (Laurent et al., "Encoding of olfactory information with oscillating neural assemblies," Science, 1994, pp. 1872-1875, vol. 265). The probe was inserted at a maximum speed of ~10 μm/s, and lowered to a final depth of 250-300 μm with respect to the tip, corresponding to approximately the length of the antennal lobe, as well as the full span of the electrode array. Recordings were performed at several intervals during insertion. Following a preliminary electrical amplification stage, the data acquisition system permitted any 16 channel combination to be selected for signal processing, which involved main stage amplification, and band pass filtering before storage for offline analysis.

Representative multisite recordings captured with one of the devices are shown in FIGS. 16A-16C. Signal processing was carried out on an algorithm using data from four simultaneously recorded channels to isolate single unit clusters (Pouzat et al., "Using noise signature to optimize spike-sorting and to assess neuronal classification quality," J Neurosci Methods, 2002, pp. 43-57, vol. 122). The closely packed arrangement of electrodes on the probes facilitates measurement of the same unit on multiple sites (FIGS. 16A-16B). This signal redundancy has been shown to improve single-unit isolation quality (Gray et al., "Tetrodes markedly improve the reliability and yield of multiple single-unit isolation from multi-unit recordings in cat striate cortex," J Neurosci Methods, 1995, pp. 43-54, vol. 63). On the other hand, the rapid spatial decay of extracellular fields ensured that only a small number of neighboring channels was located close enough to the spiking cell to exceed the spike amplitude detection threshold, which was about 50 µV in the measurements described herein. However, by aligning and averaging the waveforms of several hundred action potential events (Rutishauser et al., "Online detection and sorting of extracellularly recorded action potentials in human medial temporal lobe recordings, in vivo," *J. Neurosci. Methods,* 2006, pp. 204-224, vol. 154), strongly attenuated, but nonzero mean extracellular fields, were observed at several points in the microelectrode array.

Figure 17:
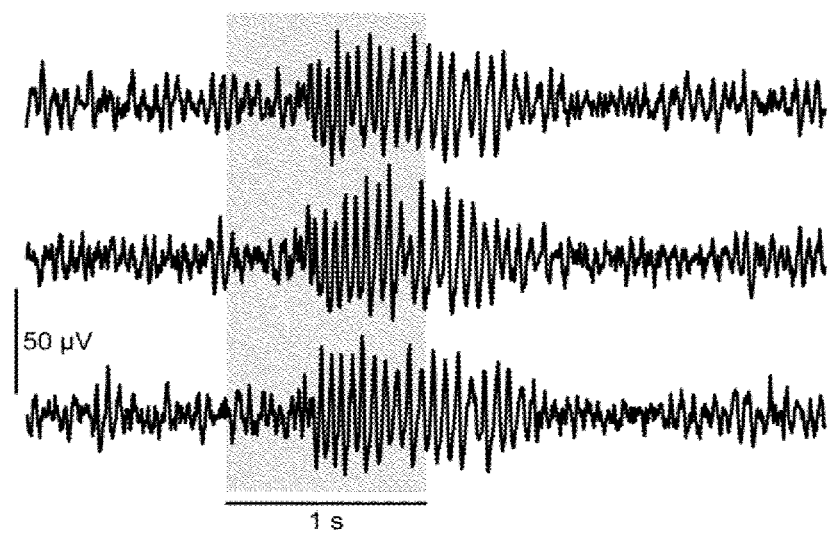
FIG. 17 shows local field potentials (LFP) in the locust body measured at a recording site on a dual-side probe array. The gray bar denotes a one second cis-3-hexanol odor presentation. Data represent three consecutive single-channel trials, filtered from 5 to 300 Hz.

Raster plots of two projection neurons measured in parallel are shown in FIG. 16C. As a further demonstration of the probe's recording functionality, local field potential (LFP) was measured in the body (FIG. 17), displaying characteristic odor-evoked oscillations. The odor-evoked responses of single units and LFP signals were found to be qualitatively similar to previous studies employing extracellular measurements in the locust (Perez-Orive et al. 2002).

Results

Dual-Side Electrode Array and Process

This process was performed in addition to the single-sided process described above. The next two steps in the sequence involved metallization on both sides using the etched alignment marks. As FIG. 5A shows, the fabrication can take place at the whole wafer level, resulting in a high-yield process. The remaining steps proceeded in the same fashion as for single-sided devices described above and were mirrored on the back side. The process yielded devices with back side feature alignment equal to or better than 10 µm. FIGS. 5B and 5C depict front and back views of a dual-side device in one embodiment. In this embodiment, the features on the back were misaligned by a small amount, leading to the overhanging oxide as seen in FIG. 5C.

Figures 18A, 18B:
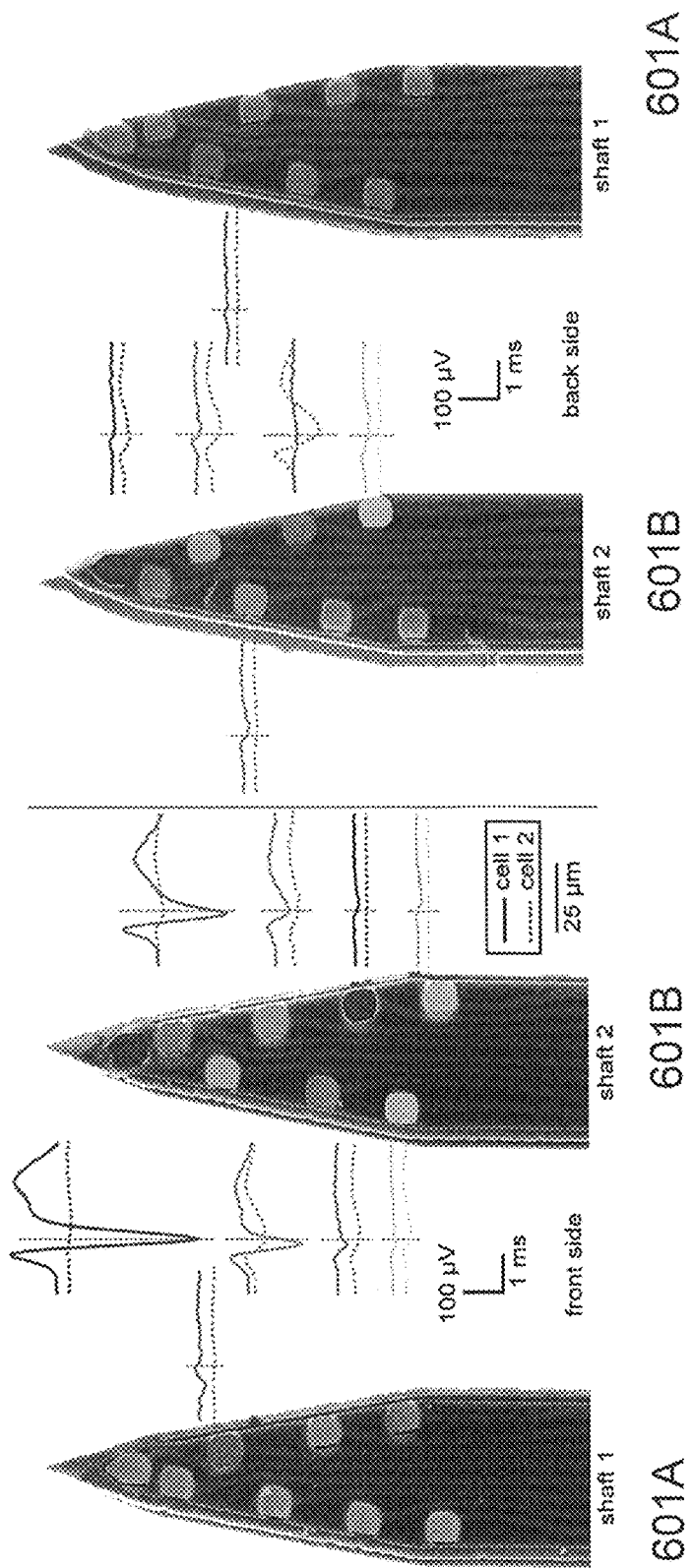
FIGS. 18A-18B show spiking activity that can be measured in parallel on both front (FIG. 18A) and back (FIG. 18B) sides of a dual-side microelectrode array. Cell 1 waveforms (solid lines) represent the average of 96 spikes that are more strongly picked up on the front, while cell 2 waveforms (dashed lines) represent the average of 430 spikes that are mainly picked up on the back. For clarity, some solid and dashed plots are offset along the vertical axis. As a spatial reference, waveforms are plotted beside an edited electron micrograph of a representative device. Each functional electrode is color-tone matched according to its corresponding waveform. Unshaded electrodes are not used in the recordings. Dashed vertical gray lines denote the same time point for each unit.

Measurements were obtained with a device using the dual-side array geometry that is depicted in FIGS. 15A-15C. The traces in FIGS. 18A-18B show the noise-averaged spike waveforms from two putative projection neurons that are measured simultaneously on the front and back sides of the probe. Signals from the first unit (probe 601A, solid lines) were picked up most strongly on the front, with almost no signal on the back side. Moreover, signals from the second unit (probe 601B, dashed lines) appear more prominently on the back, although some channels on the front register a significant amplitude signal. As the spike detection threshold was around 50 µV, it appears that spikes from cell 1 were detected from only one side, while those from cell 2 were detected from both sides.

The results showed two benefits of using dual-side electrode arrays: first, under conditions of strong signal attenuation between the front and back side (e.g, cell 1), the probability of detecting a spiking neuron in the vicinity of the probe can be increased. Second, under conditions of moderate attenuation (e.g., cell 2), signals impinging on both sides may be exploited to improve single unit isolation (Gray et al., "Tetrodes markedly improve the reliability and yield of multiple single-unit isolation from multi-unit recordings in cat striate cortex," *J Neurosci Methods,* 1995, pp. 43-54, vol. 63).

Multilayer Device

FIGS. 19A-19C show a simple multilayer probe arranged in a 2×2 shaft configuration, which comprises two silicon probes 601A, 601B. The individual device layers were identical to the structures in FIGS. 15A and 15B, but flip-chip bonded on either side of a 100 µm thick PCB 603 (FIG. 19C). The PCB connected to two sets of inward facing 16-channel arrays. Each layer in the structure was therefore capable of receiving extracellular signals from the same volume of tissue, but from opposite directions. Single-unit spiking activity captured with the multilayer array was shown in FIG. 20, comprising a plurality of representative probes 601A, 601B. The strongest signals originate near the lower right shaft, but the noise-averaged waveforms showed strongly attenuated but persistent extracellular potentials across distances exceeding 100 µm along multiple directions. Furthermore, the results showed markedly different spatial dependence of the potential along the different sampling planes. A qualitative comparison of these observations with models of extracellular potential around a spiking neuron (Gold et al., "On the origin of the extracellular action potential waveform: a modeling study," *J Neurophysiol,* 2006, pp. 3113-3128, vol. 95), suggest extensive neuronal arborization along three dimensions. This is consistent with the radial secondary dendritic geometry of antennal lobe projection neurons (Laurent et al., "Odorant-induced oscillations in the mushroom bodies of the locust," *J Neurosci,* 1994, pp. 2993-3004, vol. 14).

In addition to recording extracellular fields, the neural probes should enable electrical stimulation of local brain circuits.

Radial Distance Dependence of Extracellular Fields

The close electrode spacing enables an evaluation of the spatial decay of extracellular action potential fields within 3D arrays of probes described herein. This analysis may be useful for relating biophysical neuron models to actual recordings (Gold et al., "On the origin of the extracellular action potential waveform: a modeling study," *J Neurophysiol,* 2006, pp. 3113-3128, vol. 95). The results of FIGS. 18A-18B and 20 illustrate that extracellular fields change rapidly in space in the presumed vicinity of the soma (Henze et al., "Intracellular features predicted by extracellular recordings in the hippocampus in vivo," *J Neurophysiol,* 2000, pp. 390-400, vol. 84), but also that fields measured from each cell appear to exhibit a high level of variability due to expected differences in cellular position relative to the array.

Figure 21:
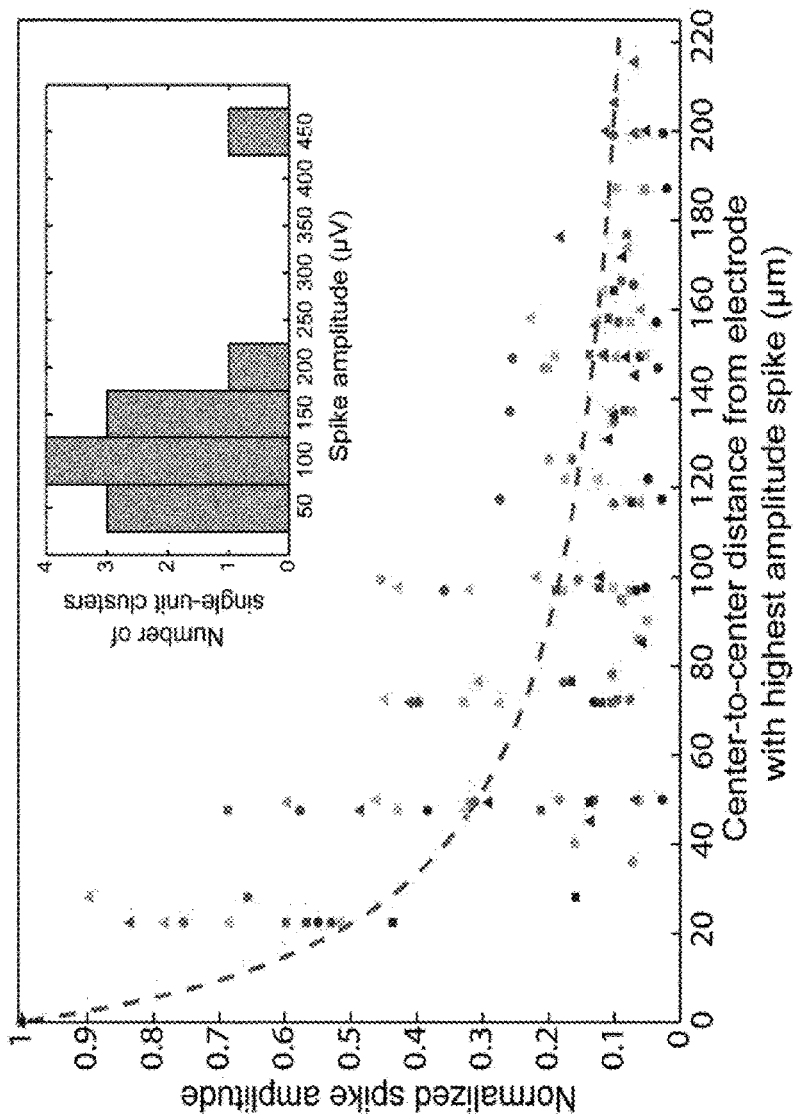
FIG. 21 is a plot of spike amplitude versus distance which shows extracellular action potential fields which decay in space. Normalized spike amplitude is plotted as a function of distance from the electrode displaying the largest signal. The origin (i.e., x=0) is not the same for all cells. Different symbols refer to different cells. The dashed curve is a fit to the data using Eqn. 2, which gives a characteristic decay length of $\lambda=22\pm3$ μm. The inset is a histogram of the maximum measured spike amplitude of all single units recorded with the dual-side and multilayer array devices.

FIG. 21 shows the normalized spike amplitude as a function of separation from the site of maximum measured amplitude, calculated independently for all projection neurons recorded during testing of the dual-side and multilayer arrays. On average the normalized extracellular signal is found to be roughly inversely proportional to distance. The normalized signal measured by an electrode can be approximated as:

$$V/V_0 = (1+x/\lambda)^{-1} \quad (2)$$

where x is the radial distance from the electrode. This expression is consistent with an electrostatic field model that assumes radial symmetry and isotropic fluid conductivity (see Gold et al., "On the origin of the extracellular action potential waveform: a modeling study," *J Neurophysiol,* 2006, pp. 3113-3128, vol. 95). However, an important distinction is that the frame of reference herein is centered on the recording site rather than the neuron, whose precise position remains unknown. The normalization constant $V_0$ reflects the maximum measurable spike amplitude averaged over the entire ensemble of recorded neurons (see inset of FIG. 21), which equals ~150 µV. The characteristic decay length of extracellular fields is represented by $\lambda$, which is 22±3 µm from a fit of Eqn. 2 to the data points in FIG. 21.

Based on these observations, it is inferred that the difference in single unit signals seen between the front and back of the dual-side array may partly be justified in terms of the nonzero thickness of the silicon structure and spatial decay of extracellular fields. However, electric fields may be appreciably distorted at the boundary between the device and extracellular fluid, likely resulting in significant signal shielding for certain neuron-electrode arrangements (Moffitt et al., "Model-based analysis of cortical recording with silicon microelectrodes," *Clinical Neurophysiol.*, 2005, pp. 2240-2250. vol. 116).

The foregoing description of the embodiments of the invention has been presented for purposes of illustration and description. It is not intended to be exhaustive or to limit the invention to the precise form disclosed, and modifications and variations are possible in light of the above teaching or may be acquired from practice of the invention. The embodiments were chosen and described in order to explain the principles of the invention and as a practical application to enable one skilled in the art to utilize the invention in various embodiments and with various modification are suited to the particular use contemplated. It is intended that the scope of the invention be defined by the claims appended hereto and their equivalents.

The following references are incorporated by references in their entirety.

Bjornsson, C. S., Oh, S. J., Al-Kofahi, Y. A., Lim, Y. J., Smith, K. L., Turner, J. N., De, S., Roysam, B., Shain, W. and Kim, S. J., "Effects of insertion conditions on tissue strain and vascular damage during neuroprosthetic device insertion," *J. Neural Eng.*, 2006, pp. 196-207, vol. 3.

Blanche, T. J., Spacek, M. A., Hetke, J. F. and Swindale, N. V., "Polytrodes: High-density silicon electrode arrays for large-scale multiunit recording," Journal of Neurophysiology, 2005, pp. 2987-3000, vol. 93, no. 5.

Bragin, A., Jandó, G., Nádasdy, Z., Hetke, J., Wise, K., Buzsáki, G., "Gamma (40-100 Hz) oscillation in the hippocampus of the behaving rat," *J Neurosci*, 1995, pp. 47-60, vol. 15.

Buchwald, J. S. and Grover, F. S., "Amplitudes of background fast activity characteristic of specific brain sites," *J Neurophysiol*, 1970, pp. 148-159, vol. 33.

Buzsáki, G., "Large-scale recording of neuronal ensembles," *Nature Neuroscience*, 2004, pp. 446-451, vol. 7.

Campbell, P. K., Jones, K. E., Huber, R. J., Horch, K. W. and Normann, R. A., "A silicon-based, three-dimensional neural interface: manufacturing processes for an intracortical electrode array," *IEEE Trans. Biomed. Eng.*, 1991. pp. 758-768, vol. 38.

Chen, J., Wise, K. D., Hetke, J. F., Bledsoe Jr., S. C., "A multichannel neural probe for selective chemical delivery at the cellular level," *IEEE Trans. Biomed. Eng.*, 1997, pp. 760-769, vol. 44.

Cheung, K. C., "Implantable microscale neural interfaces," *Biomed. Microdevices*, 2007, pp. 923-938, vol. 9.

Cheung, K. C., Djupsund, K., Dan, Y. and Lee, L. P., "Implantable multichannel electrode array based on SOI technology," *J. Microelectromechanical Systems*, 2003, pp. 179-184, vol. 12.

Csicsvari, J., Henze, D. A., Jamieson, B., Harris, K. D., Sirota, A., Bartho, P., Wise, K. D. and Buzsáki, G., "Massively parallel recording of unit and local field potentials with silicon-based electrodes," *J. Neurophysiol.*, 2003, pp. 1314-1323, vol. 90.

Drake, K. L., Wise, K. D., Farraye, J., Anderson, D. J., and BeMent, S. L., "Performance of planar multisite microprobes in recording extracellular single-unit intracortical activity," *IEEE Trans. Biomed. Eng.*, 1988, pp. 719-732, vol. 35, no. 9.

Gold, C., Henze, D. A., Koch, C. and Buzsáki, G., "On the origin of the extracellular action potential waveform: a modeling study," *J Neurophysiol*, 2006, pp. 3113-3128, vol. 95.

Gray, C. M., Maldonado, P. E., Wilson, M. and McNaughton, B., "Tetrodes markedly improve the reliability and yield of multiple single-unit isolation from multi-unit recordings in cat striate cortex," *J Neurosci Methods*, 1995, pp. 43-54, vol. 63.

Harrison, R. R. and Charles, C., "A low-power low-noise CMOS amplifier for neural recording applications," *IEEE J Solid-State Circ*, 2003, pp. 958-965, vol. 38.

Henze, D. A., Borhegyi, Z., Csicsvari, J., Mamiya, A., Harris, K D., and Buzsáki, G., "Intracellular features predicted by extracellular recordings in the hippocampus in vivo," *J Neurophysiol*, 2000, pp. 390-400, vol. 84.

Hoogerwerf, A. C. and Wise, K. D., "A three-dimensional microelectrode array for chronic neural recording," *IEEE Transactions on Biomedical Engineering*, 1994, pp. 1136-1146, vol. 41, no. 12.

Ilic, B. Czaplewski, D., Neuzil, P., Stanczyk, T., Blough, J. and Maclay, G. J., "Preparation and characterization of platinum black electrodes," *J. Mat. Sci.*, 2000, pp. 3447-3457, vol. 35.

Laurent, G. and Davidowitz, H., "Encoding of olfactory information with oscillating neural assemblies," *Science*, 1994, pp. 1872-1875, vol. 265.

Laurent, G. and Naraghi, M., "Odorant-induced oscillations in the mushroom bodies of the locust," *J Neurosci*, 1994, pp. 2993-3004, vol. 14.

Logothetis, N. K., Pauls, J., Augath, M., Trinath, T. and Oeltermann, A., "Neurophysiological investigation of the basis of the fMRI signal," *Nature*, 2001, pp. 150-157, vol. 412.

Mann, E. O., Suckling, J. M., Hajos, N., Greenfield, S. A. and Paulsen, 0., "Perisomatic feedback inhibition underlies cholinergically induced fast oscillations in the rat hippocampus in vitro," *Neuron*, 2005, pp. 105-117, vol. 45.

McIntyre, C. C., Grill, W. M., Sherman, D. L. and Thakor, N. V., "Cellular effects of deep brain stimulation: model-based analysis of activation and inhibition," *J Neurophysiol*, 2004, pp. 1457-1469, vol. 91.

Moffitt, M. A. and McIntyre, C. C., "Model-based analysis of cortical recording with silicon microelectrodes," *Clinical Neurophysiol.*, 2005, pp. 2240-2250. vol. 116.

Mountcastle, V. B., "The columnar organization of the neocortex," *Brain*, 1997, pp. 701-722, vol. 120.

Najafi, K., Wise, K. D. and Mochizuki, T., "A high-yield IC-compatible multichannel recording array," *IEEE Trans Electron Devices*, 1985, pp. 1206-1211, vol. 32, no. 7.

Najafi, K. and Wise, K. D., "An implantable multielectrode array with on-chip signal processing," *IEEE J. Solid-State Circuits*, 1986, pp. 1035-1044, vol. SC-21.

Najafi, K., Li, J. and Wise, K. D., "Scaling limitations of silicon multichannel recording probes," *IEEE Trans. Biomed. Eng.*, 1990, pp. 1-11, vol. 37.

Neves, H. P., Orban, G. A., Koudelka-Hep, M., Stieglitz, T. and Ruther, P., "Development of modular multifunctional probe arrays for cerebral applications," *Proc 3rd Intl IEEE EMBS Conference Neural Eng*, 2007, pp. 104-109.

Nicolelis, M A L, Ghazanfar, A. A., Faggin, B. M., Votaw, S. and Oliveira, L M O., "Reconstructing the Engram: simultaneous, multisite, many single neuron recordings," *Neuron*, 1997, pp. 529-537, vol. 18.

Norlin, P., Kindlundh, M., Mouroux, A., Yoshida, K. and Hofmann, U. G., "A 32-site neural recording probe fabricated by DRIE of SOI substrates," *Journal of Micromechanics and Microengineering,* 2002, pp. 414-419, vol. 12, no. 4.

Olsson, R. H., Buhl, D. L., Sirota, A. M., Buzsáki, G. and Wise, K. D., "Band-tunable and multiplexed integrated circuits for simultaneous recording and stimulation with microelectrode arrays," *IEEE Trans Biomed Eng,* 2005, pp. 1303-1311, vo. 52.

Pang, C., Cham, J. G., Nenadic, Z., Musallam, S., Tai, Y. C., Burdick, J. W. and Andersen, R. A., "A new multi-site probe array with monolithically integrated parylene flexible cable for neural prostheses," 27*th Annual International Conference of the IEEE Engineering in Medicine and Biology Society,* 2005, pp. 7114-7117.

Perez-Orive, J., Mazor, O., Turner, G. C., Cassenaer, S., Wilson, R. I. and Laurent, G., "Oscillations and sparsening of odor representations in the mushroom body," *Science* 297: 359-365, 2002.

Perlin, G. E. and Wise, K. D., "The effect of the substrate on the extracellular neural activity recorded with micromachined silicon microprobes," 26*th Annual International Conference of the IEEE Engineering in Medicine and Biology Society,* 2004, pp. 2002-2005, vol. 3.

Pouzat, C., Mazor, O. and Laurent, G., "Using noise signature to optimize spike-sorting and to assess neuronal classification quality," *J Neurosci Methods,* 2002, pp. 43-57, vol. 122.

Rutishauser, U., Schuman, E. M. and Mamelak, A. N., "Online detection and sorting of extracellularly recorded action potentials in human medial temporal lobe recordings, in vivo," *J. Neurosci. Methods,* 2006, pp. 204-224, vol. 154.

Segev, R., Goodhouse, J., Puchalla, J. and Berry, M. J., "Recording spikes from a large fraction of the ganglion cells in a retinal patch," *Nature Neurosci,* 2004, pp. 1155-1162, vol. 7.

Shoham, S., O'Connor, D. H. and Segev, R., "How silent is the brain: is there a dark matter problem in neuroscience?" *J. Comp. Physiol. A.,* 2006, pp. 777-784, vol. 192.

Stieglitz, T. and Gross, M., "Flexible BIOMEMS with electrode arrangements on front and back side as key component in neural prostheses and biohybrid systems," *Sensors and Actuators B,* 2002, pp. 8-14, vol. 83.

Takeuchi, S., Suzuki, T., Mabuchi, K. and Fujita, H., "3D flexible multichannel neural probe array," *J. Micromech. Microeng.,* 2004, pp. 104-107, vol. 14.

Wise, K. D., Sodagar, A. M., Yao, Y., Ning Gulari, M., Perlin, G. E., Najafi, K., "Implantable neural microsystems," *Proc IEEE,* 2008, pp. 1184-1202, vol. 96.

Wise, K. D., "Integrated sensors, MEMS, and microsystems: Reflections on a fantastic voyage," Sensors and Actuators a-Physical, 2007, pp. 39-50, vol. 136, no. 1.

Yao, Y., Gulari, M. N., Wiler, J. A. and Wise, K. D., "A micro-assembled low-profile three-dimensional microelectrode array for neural prosthesis applications," *J. Microelectromechanical Systems,* 2007, pp. 977-988, vol. 16.

What is claimed is:

1. A method of making a neural probe using temporary adhesive attachment between a neural probe substrate and a carrier, comprising:
   providing a neural probe substrate having a thickness of 150 μm or less having a first side and having a second side;
   patterning at least one first electrode on the a first side of the substrate;
   attaching the second side of the substrate having the patterned first electrode on the first side to a carrier, wherein the attaching is carried out with an adhesive;
   patterning the substrate into the neural probe comprising at least one shaft connected to a base; and
   removing the neural probe from the carrier.

2. The method of claim 1, further comprising forming at least one second electrode on the second side of the substrate, wherein the at least one second electrode is separately addressable from the at least one first electrode.

3. The method of claim 2, further comprising forming alignment marks through the substrate and using the alignment marks to align the at least one second electrode with the at least one first electrode.

4. The method of claim 2, wherein during the forming of at least one second electrode on the second side of the substrate, the substrate is mounted to a temporary carrier on the first side of the substrate.

5. The method of claim 1, further comprising forming a layer comprising Parylene, silicon oxide, silicon nitride or polyimide over the at least one first electrode, forming a resist layer over the layer, patterning the resist layer by electron beam or UV lithography, and forming at least one opening in the layer to expose the at least one first electrode using the patterned resist layer as a mask.

6. The method of claim 1, further comprising attaching a second neural probe to the neural probe.

7. The method of claim 1, wherein the substrate comprises a silicon substrate and the neural probe is a part of an array of neural probes.

8. The method of claim 1, wherein the adhesive is a polymeric adhesive.

9. The method of claim 1, wherein the adhesive is a photoresist.

10. The method of claim 1, wherein the second side of the substrate having a thickness of 150 μm or less is temporarily bonded to a substrate carrier when patterning the at least one first electrode on the first side of the substrate.

11. The method of claim 1, wherein the second side of the substrate having a thickness of 150 μm or less is temporarily bonded to a substrate carrier with an adhesive before and when patterning the at least one first electrode on the first side of the substrate.

12. The method of claim 11, wherein before patterning the at least one first electrode on the first side of the substrate, the substrate, the adhesive, and the substrate carrier are subjected to a weight and thermal cycling.

13. The method of claim 1, wherein the carrier is thicker than 150 microns.

14. The method of claim 1, wherein the substrate is silicon.

15. The method of claim 1, wherein the substrate is silicon having two smoothly polished surfaces.

16. The method of claim 1, wherein the substrate has a thickness of less than about 50 μm.

17. The method of claim 1, wherein the substrate has a thickness of less than about 25 μm.

18. The method of claim 1, wherein patterning the substrate into the neural probe comprising at least one shaft connected to a base comprises etching the substrate all the way through its thickness with no backside thinning.

19. The method of claim 1, wherein the removed neural probe is further assembled into a larger neural probe array comprising: a first structure, comprising a first base and a first shaft extended from the first base, the first shaft comprising at least one first electrode disposed thereon; a second structure, comprising a second base and a second shaft extended from the second base, the second shaft comprising at least one second electrode disposed on thereon; and a spacer having first and second opposing sides, wherein the spacer is disposed between at least a portion of the first base and at least a portion of the second base, wherein each of the first shaft and the second shaft extends beyond an edge of the spacer, wherein the first structure is attached to the first side of a spacer, and the second structure is attached to the second, opposing side of the spacer, wherein the at least one second electrode is separately addressable from the at least one first electrode, and wherein the at least one first electrode and the at least one second electrode are configured for measuring extracellular potentials in a biological tissue.

20. The method of claim 1, wherein the removed neural probe is further assembled into a three-dimensional structure of neural probes.

\* \* \* \* \*